US00RE43281E

(19) United States
(12) Reissued Patent
Higuma et al.

(10) Patent Number: US RE43,281 E
(45) Date of Reissued Patent: Mar. 27, 2012

(54) ENDOSCOPE CAPABLE OF BEING AUTOCLAVED

(76) Inventors: Masakazu Higuma, Hachioji (JP); Yasuyuki Futatsugi, Hachioji (JP); Takeaki Nakamura, Hino (JP); Yosuke Yoshimoto, Hachioji (JP); Takahiro Kishi, Yokohama (JP); Yasuhito Kura, Hachioji (JP); Yutaka Tatsuno, Sagamihara (JP); Takao Yamaguchi, Hachioji (JP); Susumu Aono, Hachioji (JP); Ichiro Nakamura, Kokubunji (JP); Jun Hiroya, Iruma (JP); Hidetoshi Saito, Hanno (JP); Kazutaka Nakatsuchi, Hino (JP)

(21) Appl. No.: 11/108,104

(22) Filed: Apr. 15, 2005

Related U.S. Patent Documents

Reissue of:
(64) Patent No.: 6,547,721
Issued: Apr. 15, 2003
Appl. No.: 09/370,659
Filed: Aug. 6, 1999

(30) Foreign Application Priority Data

| | | |
|---|---|---|
| Aug. 7, 1998 | (JP) | 10-224822 |
| Aug. 7, 1998 | (JP) | 10-224923 |
| Aug. 27, 1998 | (JP) | 10-242036 |
| Aug. 28, 1998 | (JP) | 10-243649 |
| Aug. 28, 1998 | (JP) | 10-243650 |
| Sep. 1, 1998 | (JP) | 10-247459 |
| Sep. 8, 1998 | (JP) | 10-254263 |
| Sep. 9, 1998 | (JP) | 10-255743 |
| Jul. 22, 1999 | (JP) | 11-208128 |
| Jul. 22, 1999 | (JP) | 11-208129 |
| Jul. 22, 1999 | (JP) | 11-208131 |

(51) Int. Cl.
*A61B 1/005* (2006.01)

(52) U.S. Cl. ..... 600/133; 600/109; 600/110; 600/169

(58) Field of Classification Search ..... 600/133, 600/103, 110, 129, 130, 169; 348/65, 294, 348/340
See application file for complete search history.

(56) References Cited

U.S. PATENT DOCUMENTS 4,545,369 A * 10/1985 Sato ..... 600/133
(Continued)

FOREIGN PATENT DOCUMENTS

DE 37 08 124 9/1987
(Continued)

OTHER PUBLICATIONS

European Search Report (in English) issued Nov. 29, 1999 in a related application.*

*Primary Examiner* — John P Leubecker

(57) ABSTRACT

An endoscope capable of being autoclaved in accordance with the present invention includes an insertion unit, an internal endoscope space, and contents. The insertion unit has a soft member, which is made of a soft polymeric material, as at least part of a casing thereof. The internal endoscope space includes the internal space of the insertion unit that is formed at a first sealing level at which the internal space is sealed in a watertight manner relative to an outside. The contents include at least one hermetically sealed unit composed of a plurality of airtight partition members and formed at a second sealing level higher than the first sealing level by joining the meeting portions of the airtight partition members using an airtight joining material. All or part of the airtight partition members is stowed in the internal endoscope space. Even when high-pressure high-temperature steam permeates through the soft member of the insertion unit which is made of a polymeric material, and invades into the internal endoscope space formed at the first sealing level, the high-pressure high-temperature steam will be hindered from invading into the hermetically sealed unit included in the contents and formed at the second sealing level.

38 Claims, 17 Drawing Sheets

U.S. PATENT DOCUMENTS

| | | | | | |
|---|---|---|---|---|---|
| 4,779,613 | A | | 10/1988 | Toahihiko et al. | |
| 4,878,484 | A | * | 11/1989 | Miyagi | 600/133 |
| 5,305,736 | A | * | 4/1994 | Ito | 600/109 |
| 5,349,137 | A | * | 9/1994 | Cedrone | 174/76 |
| 5,894,369 | A | * | 4/1999 | Akiba et al. | 359/820 |
| 5,992,728 | A | * | 11/1999 | Pollack et al. | 228/122.1 |
| 6,142,930 | A | * | 11/2000 | Ito et al. | 600/109 |

FOREIGN PATENT DOCUMENTS

| | | | | |
|---|---|---|---|---|
| EP | 0842633 | | | 5/1998 |
| EP | 0842633 | A1 | * | 5/1998 |
| JP | 58-90605 | | | 5/1983 |
| JP | 5890605 | A | * | 5/1983 |
| JP | 59-129050 | | | 7/1984 |
| JP | 59129050 | A | * | 7/1984 |
| JP | 60-107819 | | | 7/1985 |
| JP | 6240413 | A | * | 2/1987 |
| JP | 62-212614 | | | 9/1987 |
| JP | 62212614 | A | * | 9/1987 |
| JP | 63-315024 | | | 12/1988 |
| JP | 63315024 | A | * | 12/1988 |
| JP | 1-12802 | | | 4/1989 |
| JP | 112802 | A | * | 4/1989 |
| JP | 03-287218 | | | 12/1991 |
| JP | 4-67445 | | | 10/1992 |
| JP | 467445 | A | * | 10/1992 |
| JP | 05-253168 | | | 10/1993 |
| JP | 5-269081 | | | 10/1993 |
| JP | 5269081 | A | * | 10/1993 |
| JP | 6-209898 | | | 8/1994 |
| JP | 6209898 | A | * | 8/1994 |
| JP | 06-347707 | | | 12/1994 |
| JP | 7-51223 | | | 2/1995 |
| JP | 7512223 | A | * | 2/1995 |
| JP | 60107819 | A | * | 7/1995 |
| JP | 08-056895 | | | 3/1996 |
| JP | 08-202017 | | | 8/1996 |
| JP | 09-192093 | | | 7/1997 |
| JP | 9-265046 | | | 10/1997 |
| JP | 09-265046 | | | 10/1997 |
| JP | 9-265047 | | | 10/1997 |
| JP | 09-265047 | | | 10/1997 |
| JP | 9265046 | A | * | 10/1997 |
| JP | 9265047 | A | * | 10/1997 |

* cited by examiner

ENDOSCOPE CAPABLE OF BEING AUTOCLAVED

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to an endoscope whose contents will resist high-temperature high-pressure steam given off during autoclaving so as not to be destroyed or deteriorated, and whose insertion unit has a soft part.

2. Description of the Related Art

Endoscopes having an insertion unit thereof inserted into a body cavity for observation of a deep region or for medical treatments to be, if necessary, conducted using a treatment appliance have been widely used in the field of medicine.

In the case of endoscopes for medical studies, disinfecting and sterilizing a used endoscope is essential for preventing infectious diseases. A sterilization gas such as an ethylene oxide (EOG) gas or a disinfectant has been used to disinfect and sterilize a used endoscope in the past.

However, sterilization gases are, as already known, quite toxic. Sterilization work cannot help becoming imperfect because it must be carried out safely. Moreover, adverse effects of a sterilization gas on an environment are in question. Since it takes much time for aeration intended to remove gas sticking on equipment after sterilization, a sterilized endoscope cannot be used immediately after sterilization. Moreover, there is a question of a high running cost.

On the other hand, disinfectants are hard to manage. Besides, the fact that a great expense is needed to dispose of a disinfectant must be taken into consideration.

Autoclaving has become a mainstream of disinfection and sterilization of endoscopic equipment these days. This is because autoclaving does not require time-consuming work, makes it possible to use equipment immediately after autoclaving, and costs a little for running.

Typical conditions for autoclaving are stipulated as the ANSI/AAMI ST37-1992 acknowledged by the American National Standards Institute and issued by the Association for the Advancement of Medical Instrumentation. The conditions define that pre-vacuum type autoclaving should be performed at 132° C. for four minutes and that gravity type autoclaving should be performed at 132° C. for ten minutes. Degrees of temperature at which autoclaving is actually performed range from 115° C. to 140° C. in general.

A typical process of pre-vacuum type autoclaving includes a pre-vacuum step, a sterilization step, and a drying step. At the pre-vacuum step, a sterilization chamber in which medical equipment to be sterilized is stowed is decompressed to exhibit a negative pressure. At the sterilization step, high-pressure high-temperature steam is injected into the sterilization chamber for sterilization. At the drying step, the sterilization chamber is decompressed again in order to dry a sterilized endoscope.

The pre-vacuum step is a step intended to facilitate infiltration of steam into the minute spaces in medical equipment which is performed at the sterilization step. The sterilization chamber is decompressed, whereby high-pressure high-temperature steam penetrates the whole of the stowed medical equipment. The pressure in the sterilization chamber to be attained at the pre-vacuum step and drying step is calculated as "an atmospheric pressure −0.07 MPa or so." The pre-vacuum step is included in a process of gaseous sterilization using an ethylene oxide gas. The pressure to be attained at the sterilization step is often set to a value calculated as "the atmospheric pressure +0.2 MPa or so."

In general, endoscopes have a soft insertion unit or are of a bendable type having a bendable part. In this case, an armor tube made of a soft polymeric material such as a rubber or elastomer is used as a casing member for the soft insertion unit or bendable part. Moreover, since the endoscopes must be immersed in a fluid agent, the endoscopes are entirely watertight.

When a watertight endoscope is autoclaved, a soft armor tube may dilate to break at the decompression step such as the pre-vacuum step. Otherwise, a joint of parts may not fail to resist a difference in pressure between the interior and exterior of the endoscope any longer, and may eventually be broken.

For preventing the above incident, Japanese Unexamined Utility Model Publication No. 1-12802 has disclosed an interior-exterior communication device for airtight endoscopes.

According to the utility model, when a process of gaseous sterilization including a pre-vacuum step is adopted, an airtightness release cap is attached to the interior-exterior communication device, which is located on the outer wall of an endoscope, at each decompression step. This is intended to allow the internal space of the endoscope (or in other words, the interior of the endoscope) to communicate with the exterior of the endoscope for preventing a burst of a bendable armor tube of a bendable part.

Moreover, Japanese Unexamined Patent Publication No. 63-315024 describes an endoscope structured so that a communication path formed in part of the outer wall of the endoscope is blocked using a waterproof cap. The endoscope is sterilized using a gas with the waterproof cap removed. It is thus prevented that an armor tube of a bendable part or the like bursts at a decompression step.

However, as far as autoclaving is concerned, the interior and exterior of an endoscope are allowed to communicate with each other, and high-pressure high-temperature steam is actively invaded into the interior. This poses a problem in that various contents of the endoscope including an observing means and internal structural members thereof deteriorate shortly because of the steam.

In efforts to cope with the problem, Japanese Examined Patent Publication No. 4-67445 has disclosed an internal pressure adjustment device for airtight endoscopes. The internal pressure adjustment device has a non-return valve mechanism located on a housing of an endoscope. The non-return valve mechanism permits passage of gas from the interior of the endoscope to the exterior thereof but prevents invasion of gas from the exterior of the endoscope into the interior thereof. Even when autoclaving is performed, it is prevented that high-pressure high-temperature steam actively invades into the interior of the endoscope.

However, an endoscope may include members made of a polymeric material such as a plastic or rubber. In this case, when the endoscope is autoclaved, high-pressure high-temperature steam permeates through the polymeric members and invades into the interior of the endoscope. In other words, unless all members constituting an endoscope are made of a raw material such as a metal, ceramic (in a broad sense, including a glass), or crystalline material, and assembled without a gap, high-pressure high-temperature steam will invade into the interior of the endoscope during autoclaving.

The Japanese Examined Patent Publication No. 4-67445 has disclosed an endoscope having a non-return valve mechanism. If the endoscope is an endoscope with a bending ability whose insertion unit has a bendable part, the bendable part is sheathed with an armor tube made of a polymeric material such as a soft rubber or elastomer. High-pressure high-temperature steam permeates through the armor tube and gradually invades into the interior of the endoscope.

Moreover, in the endoscope with a bending ability, a rubber-sealing member made of a polymeric material such as an O ring is used as a sealing member for sealing an axis of rotation of a bending lever used to bend the bendable part. High-pressure high-temperature steam used for autoclaving permeates through the rubber-sealing member and gradually invades into the interior of the endoscope.

Furthermore, even when an insertion unit of an endoscope does not have the bending ability, if the whole insertion unit is soft, a polymeric material is used to make the armor tube of the insertion unit. During autoclaving, high-pressure high-temperature steam permeates through the armor tube and gradually invades into the interior of the endoscope.

Endoscopes referred to as airtight endoscopes include endoscopes having a bending ability and endoscopes each of which insertion unit is soft. In these endoscopes, high-pressure high-temperature steam given off during autoclaving, as mentioned above, permeates through a member made of a polymeric material and gradually invades into the interior of the endoscope.

The phenomenon that steam invades into the interior of an endoscope takes place during autoclaving irrespective of whether the autoclaving is of a pre-vacuum type or gravity type.

When steam invades into the interior of an endoscope, there arises a fear that various contents of the endoscope including an observing means and internal structural members thereof may deteriorate, though gradually.

An electronic endoscope will be taken for instance. Steam invading into the interior of the endoscope may condense on the surface of a lens included in an objective unit incorporated in an imaging unit or the internal surface of a cover glass of the objective unit. Moreover, electronic parts including a solid-state imaging device may malfunction. In either case, there arises a possibility that invading steam impairs the quality of a view.

Moreover, when steam invading into the interior of an endoscope reaches an observation optical system, the steam may condense on the surface of a lens included in the observation optical system or the internal surface of a cover glass of the observation optical system to narrow a field of view. This is not limited to the electronic endoscope, but the same applies to a fiberscope.

Furthermore, a multi-component glass that can be machined readily is a lens glass widely used as the foregoing lens or cover glass. The multi-component glass deteriorates when exposed to high-pressure high-temperature steam given off during autoclaving. When steam invades into the interior of an endoscope, the glass itself may deteriorate or a coating formed on the surface of the lens or an adhesive applied to the surface thereof may deteriorate. This may impair the quality of a view.

Japanese Unexamined Patent Publication No. 62-212614 describes an endoscope in which at least part of an optical system is structured hermetically in order to prevent invasion of steam into the optical system. However, the endoscope has optical members including a lens and cover glass bonded to a frame using an adhesive. When autoclaving is performed under the conditions stipulated by the American National Standards Institute and others, steam invades into the optical system through the adhesive. In short, the structure cannot hinder invasion of high-pressure high-temperature steam in practice.

Under the foregoing conditions for autoclaving, high-pressure high-temperature steam permeates through a layer of a hardened adhesive whose major component is a polymeric material, such as, a generally adopted epoxy adhesive or silicone adhesive.

Moreover, the strength of a joint secured with the above adhesive is not so high as that of a joint secured by performing welding. When parts made of different materials, for example, a metal and glass are joined using an adhesive, the coefficient of thermal expansion differs between the parts. When the parts change due to heat during autoclaving, the joint of the parts is stressed. Consequently, the adhesive may peel off.

In consideration of the foregoing drawbacks, a rigid endoscope having a rigid insertion unit has, as described in Japanese Unexamined Patent Publication No. 9-265046, a cover glass hermetically locked in a sleeve, which is one of parts constituting a housing of the endoscope, without a gap by performing soldering. A housing structure serving as the housing of the endoscope is thus sealed hermetically.

However, in the case of an endoscope whose insertion unit has a bendable part or whose insertion unit is at least partly soft, a member made of a polymeric material is used as at least part of a housing of the endoscope. Even if only the distal part of the insertion unit has members thereof joined hermetically, the whole of the housing of the endoscope cannot be sealed fully hermetically.

In other words, the endoscope whose housing can be sealed hermetically as described in the Japanese Unexamined Patent Publication No. 9-265047 is limited to rigid endoscopes not having the bending ability and making it possible to make an insertion unit thereof using a metal or ceramic.

SUMMARY OF THE INVENTION

An object of the present invention is to provide an endoscope capable of producing a high-quality view and resisting high-pressure high-temperature steam. Specifically, during autoclaving, high-pressure high-temperature steam may permeate through an armor tube made of a polymeric material and used to outline at least part of an insertion unit, and invade into the interior of the endoscope. Nevertheless, it can be prevented that the invading steam fogs an optical system to adversely affect observation or that electronic parts or the like deteriorate.

Another object of the present invention is to provide an endoscope that will not offer a field of view narrowed due to a degraded optical system or fogging. Specifically, it can be prevented that high-pressure high-temperature steam invades into an optical system in the endoscope during autoclaving.

Still another object of the present invention is to provide an endoscope capable of being autoclaved. Specifically, it is prevented that incident light reflects from a coating covering the outer circumference of an optical member to cause flare.

Briefly, an endoscope capable of being autoclaved in accordance with the present invention includes an insertion unit, an internal endoscope space, and contents. The insertion unit has a soft member, which is made of a soft polymeric material, as at least part of a casing thereof. The internal endoscope space includes the internal space of the insertion unit which is formed at a first sealing level at which the internal space keeps watertight relative to an exterior. The contents are formed with a plurality of airtight partition members all or part of which is stowed in the internal endoscope space. The contents include at least one hermetically sealed unit made by joining the airtight partition members using an airtight joining means, and thus formed at a second sealing level higher than the first sealing level.

BRIEF DESCRIPTION OF THE DRAWINGS

FIG. 1 to FIG. 10 relate to a first embodiment of the present invention;

FIG. 1 is an explanatory diagram concerning the configuration of an electronic endoscope;

FIG. 2 is a cross sectional view for explaining the structure of a non-return valve cap;

FIG. 3 is a longitudinal sectional view for explaining the structure of the distal part of the electronic endoscope and its neighborhood;

FIG. 4 is a longitudinal sectional view for explaining the structure of an imaging unit;

FIG. 6 is an explanatory diagram concerning the distal cover glass covered with the metal coating having a low reflectance layer;

FIG. 7 is an explanatory diagram concerning a metal coating formed on the outer surface of an isolating frame;

FIG. 9 is an explanatory diagram concerning a procedure of assembling lenses to produce an objective unit included in an imaging unit;

FIG. 10 is an explanatory diagram concerning a hermetically sealed objective unit;

FIG. 16 is a longitudinal sectional view for explaining the structure of the distal part of an electronic endoscope and its neighborhood;

FIG. 17 is a longitudinal sectional view for explaining the structure of an imaging unit;

FIG. 23 is an explanatory diagram concerning the configuration of an endoscope;

FIG. 24 is a longitudinal sectional view for explaining the structure of the distal part of the endoscope and its neighborhood;

FIG. 25 is a longitudinal sectional view for explaining the structure of an eyepiece unit of the endoscope;

DESCRIPTION OF THE PREFERRED EMBODIMENTS

Referring to FIG. 1 to FIG. 10, a first embodiment of the present invention will be described below.

Figure 1:
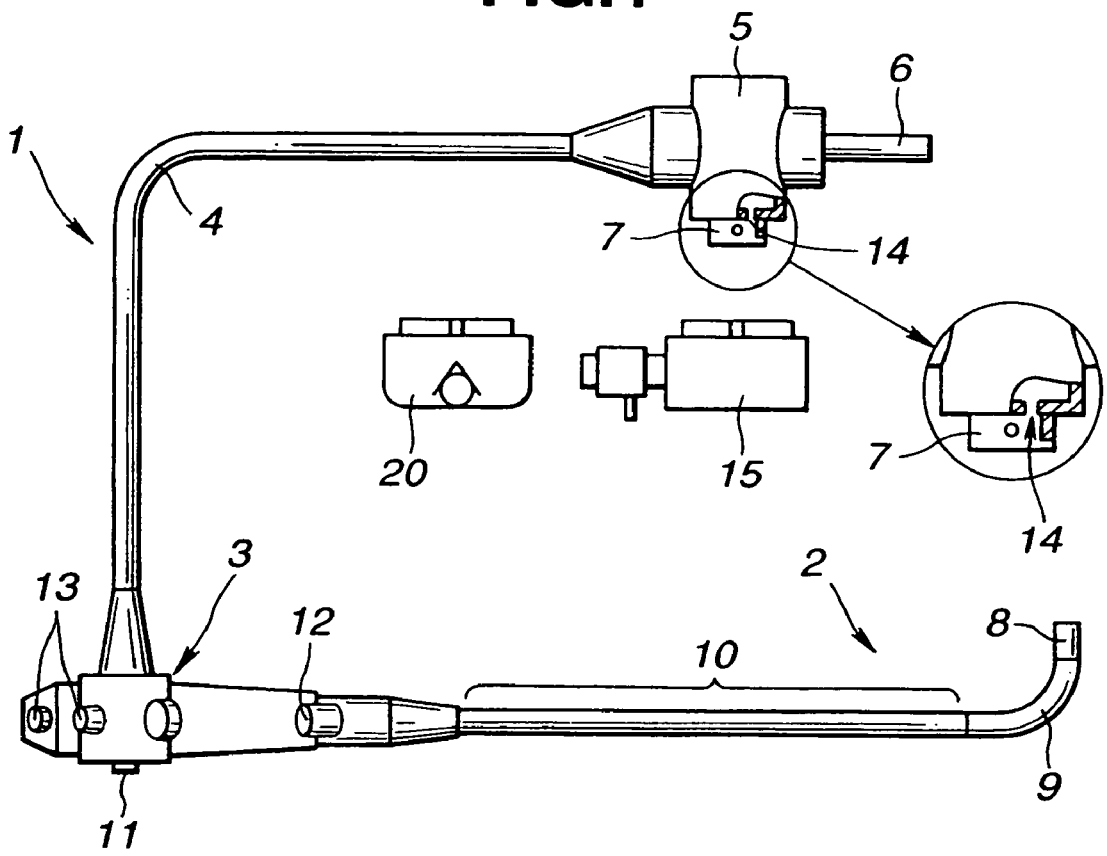

As shown in FIG. 1, an electronic endoscope 1 of this embodiment consists of different sections, mainly of an insertion unit 2, an operation unit 3, and a universal cord 4. The insertion unit 2 has a solid-state imaging device, for example, a charge-coupled device (CCD) incorporated in the distal part thereof. The operation unit 3 is coupled to the proximal end of the insertion unit 2, and held by an observer to be manipulated in various manners. The universal cord 4 extends from the operation unit 3. A connector unit 5 is attached to the other end of the universal cord 4. The connector unit 5 is connected to a light source apparatus that is not shown and a camera control unit (hereinafter abbreviated to a CCU) that is not shown.

A light guide connector 6 is connected to the light source apparatus, and a camera connector 7 is connected to the CCU. Moreover, the internal spaces of the insertion unit 2, operation unit 3, universal cord 4, and connector unit 5 communicate with one another. In other words, the internal spaces constitute one internal endoscope space (or simply an internal space) inside a housing of the endoscope.

The insertion unit 2 consists of a distal part 8, a bendable part 9 that can be bent freely, and a flexible tube 10 having flexibility.

The operation unit 3 has a bending lever 11, a treatment appliance insertion port 12, and a plurality of switches 13. The bending lever 11 is used to control the movements of the bendable part 9. The treatment appliance insertion port 12 is a port through which a treatment appliance such as forceps is inserted. The switches 13 are used to freeze or release an image. The bending lever 11 can be rotated freely and mounted together with an O ring, which is not shown, in order to attain watertightness.

The camera connector 7 has a vent 14 through which the internal space is ventilated with outside air. A waterproof cap 15 can be attached or detached to or from the camera connector 7. The waterproof cap 15 is attached to the camera connector 7, whereby the internal space of the endoscope 1 is set to a sealing level (referred to a first sealing level) at which it is sealed in a watertight manner. When the waterproof cap 15 is detached, the interior and exterior of the endoscope 1 with respect to the endoscope housing or the internal space and exterior thereof communicate with each other.

The waterproof cap 15 is attached to the camera connector 7 in order to clean the used endoscope 1 or immerse it in a fluid agent. The waterproof cap 15 seals the internal space of the endoscope 1 in a watertight manner for fear that a fluid may invade into the internal space thereof during cleaning under running water or immersion in a fluid agent. A non-return (oneway) valve cap 20 having the capability of a non-return valve can also be attached or detached to or from the camera connector 7. The non-return valve cap 20 permits passage of gas from the internal space of an endoscope to the exterior thereof but hinders passage of gas from the exterior of the endoscope to the interior thereof.

Figure 2:
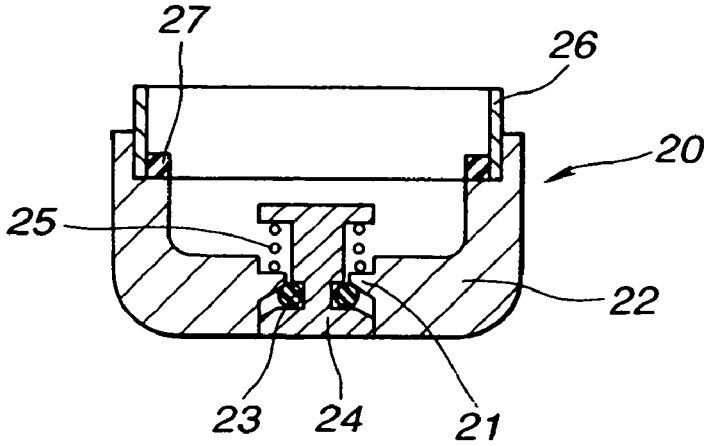

As shown in FIG. 2, the non-return valve cap 20 consists of a non-return valve cap body 22, a valve body 24, a spring 25, an attachment portion 26, and a sealing member 27. The non-return valve cap body 22 has a valve seat 21 and is made of, for example, a metal. The valve body 24 has a rubber sealing member 23 united therewith and is made of, for example, a metal. The spring 25 constrains the valve body 24 to move towards the valve seat 21. The attachment portion 26 is attached to the camera connector 7 and made of, for example, a metal. When the attachment portion 26 is attached to the camera connector 7, the sealing member 27 made of, for example, a rubber sustains the watertightness attained between the inner circumference of the attachment portion 26 and the outer circumference of the camera connector 7.

For autoclaving the endoscope 1, the non-return valve cap 20 rather than the waterproof cap 15 is attached to the camera connector 7. By attaching the non-return valve cap 20, high-pressure high-temperature steam given off during autoclaving is hindered from invading through the vent 14.

A constraining force exerted by the spring 25 is set to a magnitude of force causing the sealing member 23 to meet closely the valve seat 21 under the condition that: the valve body 24 is constrained to move towards the valve seat 21 in a normal state in which the non-return valve cap 20 is attached to the camera connector 7. Moreover, the magnitude of force allows the valve body 24 to be released from constraint causing it to move towards the valve seat 21 at a decompression step included in a process of autoclaving.

As long as the internal pressure of the internal space of the endoscope 1 does not exceed an atmospheric pressure, or in other words, in a normal use situation, the internal space of the endoscope 1 is retained at the first sealing level by attaching the non-return valve cap 20. At this time, the first sealing level is attained relative to outside air. For cleaning the endoscope 1 or immersing it in a fluid agent, the non-return valve cap 20 rather than the waterproof cap 15 may be attached.

Figure 3:
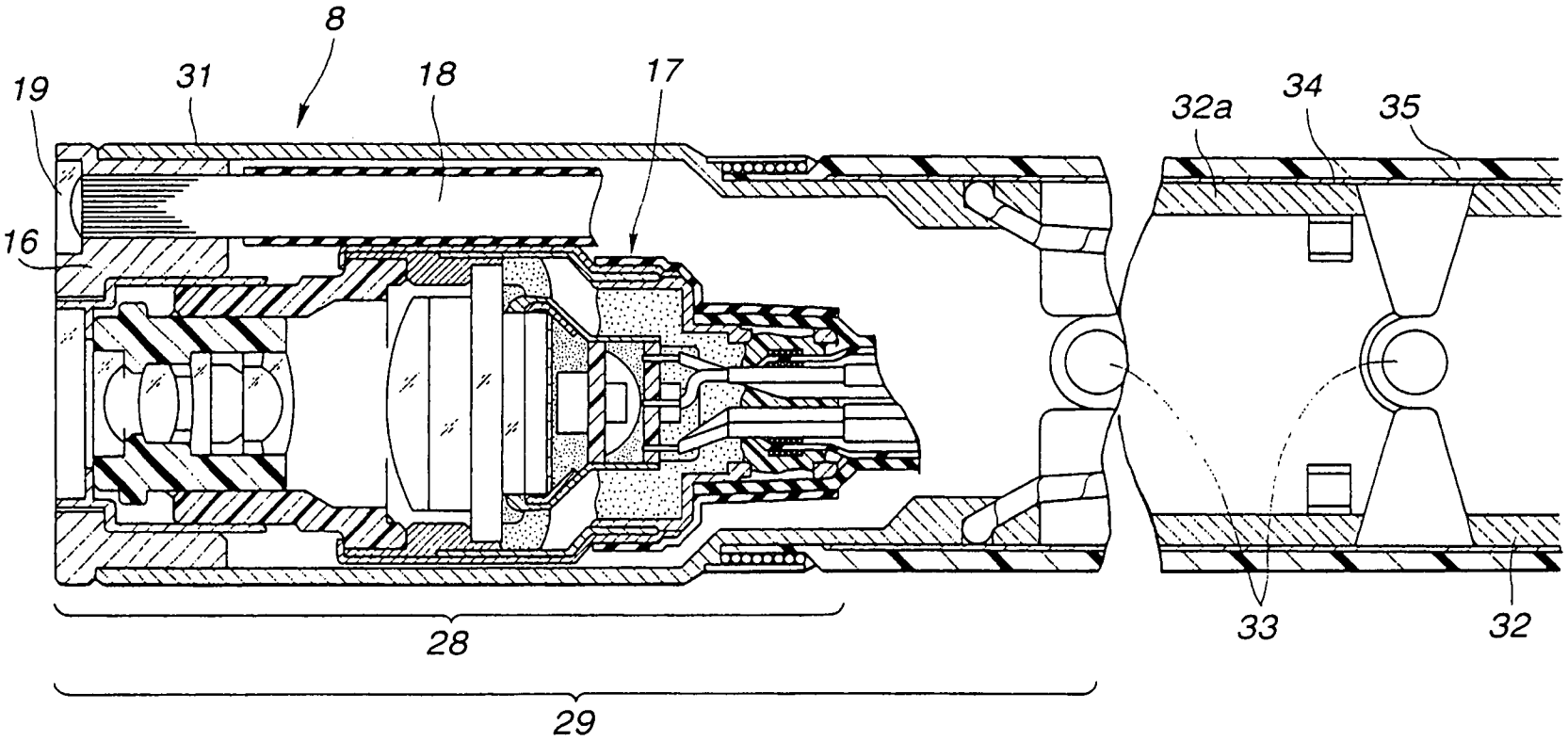

As shown in FIG. 3, an imaging unit 17 serving as an observing means and image transmitting means and a light guide fiber bundle 18 over which illumination light is transmitted are incorporated in a distal body 16 outlining the distal part 8 of the endoscope 1. An illumination lens 19 is placed on the distal surface of the light guide fiber bundle 18, and bonded and fixed to the distal body 16 using an adhesive.

A distal cover member 31 is mounted on the outer circumference of the distal body 16. A first bending piece 32a is located at the foremost position among a plurality of bending pieces 32 constituting the bendable part 9. The first bending piece 32a is coupled to the proximal end of the distal cover member 31 by a rivet 33 so that the first bending piece 32a can pivot freely. The plurality of bending pieces 32 is concatenated to the proximal end of the first bending piece 32a by the rivets 33 so that they can pivot freely. The outer circumferences of the bending pieces 32 are sheathed with a metallic meshed tube 34 and an armor tube 35. The armor tube 35 is made of a polymeric material such as a rubber or elastomer having flexibility, for example, a fluorine-contained rubber.

A range 28 covered by the imaging unit 17 corresponds to the length of a distal rigid part and falls within a distal rigid length distal to the rivet 33 located at the foremost position, that is, a range 29.

Figure 4:
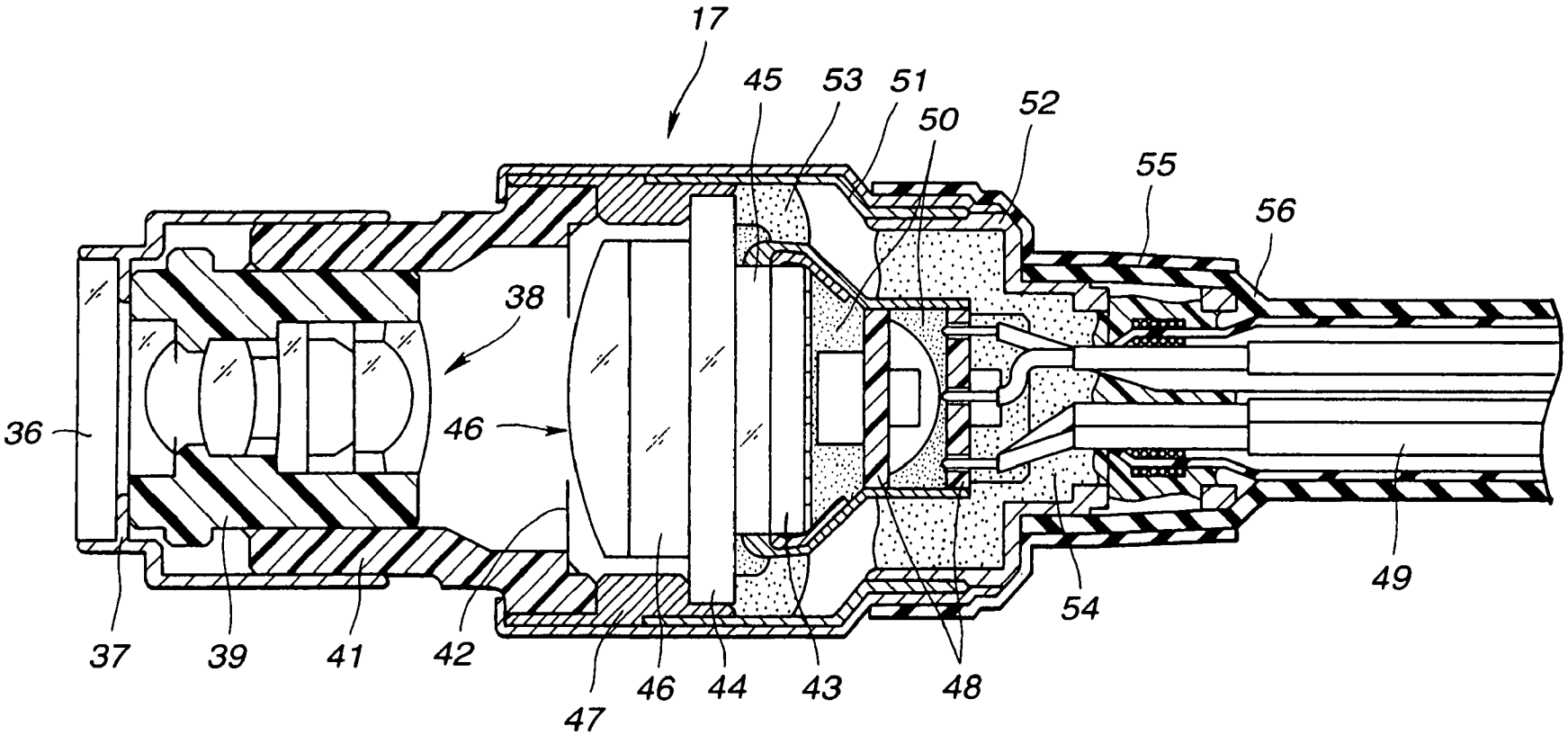

As shown in FIG. 4, a distal cover glass 36 forming an optical window of an observing means is included as part of the casing of the insertion unit 2 (in this embodiment, part of the distal surface) and placed at the tip of the imaging unit 17.

The distal cover glass 36 is made of sapphire that is highly strong, resistive to high-pressure high-temperature steam, and made into an airtight partition member, or a glass resistive to high-pressure high-temperature steam. Metal coating that is one kind of surface finishing is performed on the outer circumference of the distal cover glass 36. The distal cover glass 36 is hermetically locked inside the inner circumference of a metallic distal frame 37 without a gap using an airtight joining means. The metallic distal frame 37 is an airtight partition member resistive to high-temperature steam. The airtight joining means enables highly strong joining but does not deteriorate even when exposed to steam. Depending on how to design an optical system, a lens may be used as the optical window instead of the cover glass. The distal frame 37 is made of a stainless steel or covar.

A plate layer is formed on the internal circumference of the distal frame 37 by performing, for example, electroplating. The plate layer is composed of, for example, a lower layer of a nickel plate layer and an upper layer of a gold plate layer.

A lens frame 39 accommodating a group of objectives 38 is mounted at the proximal end of the distal cover glass 36. The group of objectives 38 includes a plurality of optical lenses and forms an image of an object. The lens frame 39 is bonded and fixed to the distal part of an isolating frame 41 serving as an airtight partition member resistive to high-pressure high-temperature steam and made of an insulating material such as ceramic. The isolating frame 41 is made of one of ceramics exhibiting a high coefficient of thermal conductivity and being strong to thermal shock. Moreover, an aperture stop plate 42 is bonded and fixed to the internal circumference of the proximal part of the isolating frame 41.

A CCD 43 is a solid-state imaging device on which an object image formed by the group of objectives 38 is projected. The CCD 43 is positioned using a reticle or the like, and bonded and fixed to a proximal cover glass 44 made of sapphire or a glass resistive to high-pressure high-temperature steam. The proximal cover glass 44 is a kind of optical window opposed to the proximal surface of the group of objectives 38. In the present embodiment, a CCD cover glass 45 is placed on the front surface of an imaging chip of the CCD 43. A lens included in a group of lenses 46 is positioned, and bonded and fixed to the distal surface of the proximal cover glass 44.

The outer circumference and chamfers of the proximal cover glass 44 have undergone the same surface finishing as the distal cover glass 36. The proximal cover glass 44 is hermetically locked in a frame body 47 formed with a metallic member, which is an airtight partition member resistive to high-pressure high-temperature steam, using an airtight joining means that will be described later. There is a gap between the outer circumference of the group of lenses 46 and the inner circumference of the frame body 47. The gap is intended to prevent the frame body 47 from stressing the joined surfaces of the lenses when the frame body 47 and group of lenses 46 exhibiting different coefficients of thermal expansion thermally expand due to heating occurring during autoclaving.

The distal part of the frame body 47 and the proximal part of the isolating frame 41 are hermetically joined using an airtight joining means. The frame body 47 is, like the distal frame 37, made of stainless steel or covar. The frame body 47 has the same plate layer as the distal frame 37 formed on the inner circumference thereof.

Moreover, when a gap between each pair of the distal cover glass 36 and distal frame 37, the distal frame 37 and isolating frame 41, and the isolating frame 41 and frame body 47 is closest to nil, the engagements of the pairs are accomplished reliably.

Moreover, there is a gap of a proper dimension between the proximal cover glass 44 and frame body 47.

The CCD 43 is electrically coupled to a cable 49 via substrates 48. Electronic parts including ICs and capacitors are mounted on the substrates 48. These electronic parts are sealed and locked using a sealing member such as an adhesive 50 having an insulation property.

The CCD 43 and others are enclosed in a first shielding frame 51 made of a metal. The first shielding frame 51 is mounted unitedly on the outer circumference of the frame body 47 by performing bonding or welding. Moreover, a second shielding frame 52 made of a metal is attached to the proximal part of the first shielding frame 51 by performing bonding or welding.

A space created by the first shielding frame 51, CCD 43, and proximal cover glass 44 is filled with a filler 53. The filler 53 is an adhesive, sealant, or a potting material that is less permeable to steam.

Moreover, an adhesive 54 is injected to the surroundings of the portion of the cable 49 lying in the second shielding frame 52. The outer circumference of the second shielding frame 52 is sheathed with thermo-contractile tubes 55 and 56 made of, for example, a fluorocarbon resin less permeable to steam.

When members are bonded to each other using an adhesive that is not shown, the adhesive may readily or hardly peel off during autoclaving depending on the material made into the members.

When an optical member is bonded and fixed to a metallic frame, since the coefficient of thermal expansion differs greatly between the metal and optical member, an adhesive may peel off. This is because the joint of the optical member and metallic frame is greatly stressed due to a difference in the coefficient of thermal expansion when a high temperature is attained during autoclaving.

By contrast, when identical members, for example, metallic members are bonded and fixed using an adhesive, since the joint of the members hardly undergoes a stress stemming from a difference in the coefficient of thermal expansion, the adhesive will not peel off. Moreover, a portion filled with an adhesive hardly undergoes a stress stemming from a difference in coefficient of thermal expansion. The adhesive therefore rarely peels off or cracks.

In the present embodiment, consideration is taken into the foregoing facts. When members constituting a portion susceptible to invasion of steam must be secured using an adhesive, members having the same coefficient of thermal expansion or members whose coefficients of thermal expansion are similar (having a small difference) are bonded and fixed to each other using an adhesive. If the members to be joined do not have the same or similar coefficient of thermal expansion, an adhesive is used for a filling within the members near the joints. Consequently, an adhesive applied to such joints hardly peels off. Even joining using an adhesive can therefore suppress permeation of steam.

Next, metal coating and airtight joining will be described with reference to FIG. 5A to FIG. 8.

Figure 5A:
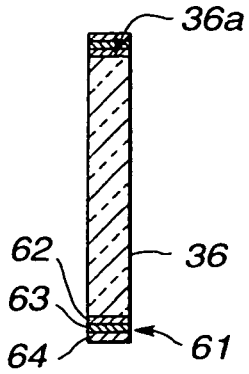
FIG. 5A is an explanatory diagram concerning a metal coating formed on a distal cover glass.
Figure 5B:
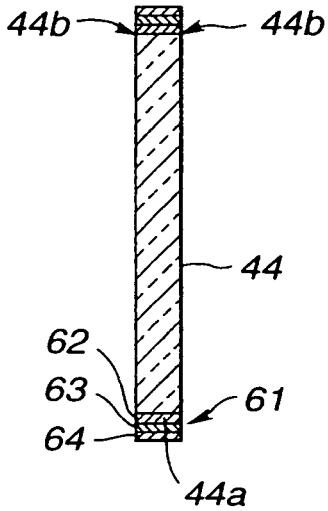
FIG. 5B is an explanatory diagram concerning a metal coating formed on a back-end cover glass.

Metal coating is performed as surface finishing in order to form a first metal coating 61 over the lateral surface 36a of the distal cover glass 36 shown in FIG. 5A and the lateral surface 44a and chamfers 44b of the proximal cover glass 44 shown in FIG. 5B.

The first metal coating 61 is composed of a chromium layer 62, a nickel layer 63, and a gold layer 64. The chromium layer 62 is a lowermost layer formed as a metallized layer. The nickel layer 63 is the second layer or an intermediate layer. The gold layer 64 is an uppermost layer and serves as a joint layer. The layers are produced by performing deposition, spattering, or plating in a vacuum.

Figure 6:
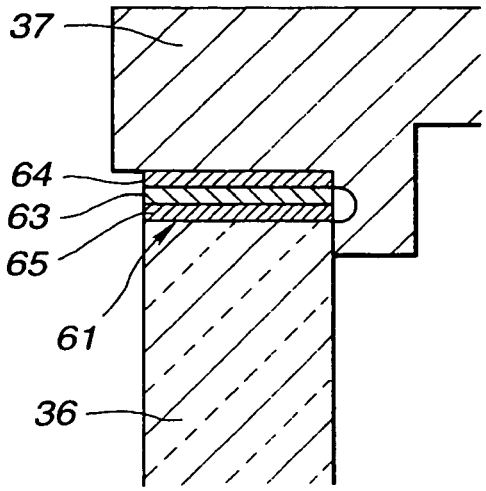

Furthermore, as shown in FIG. 6, the lowermost layer of the distal cover glass 36 may be a chromium oxide ($Cr_2O_3$) layer 65 that is a low reflectance layer. Rays reaching the chromium oxide layer 65 that is the low reflectance layer formed on the outer circumference of the cover glass 36 will hardly be reflected. Consequently, occurrence of flare or the like can be prevented, and the optical characteristic of the endoscope improves.

When the chromium oxide layer 65 is formed, the nickel layer 63 and gold layer 64 are, as illustrated, overlaid the chromium oxide layer 65. Thus, the first metal coating 61 is realized. Otherwise, the chromium layer 62, nickel layer 63, and gold layer 64 may be overlaid a chromium oxide layer 134, thus realizing the first metal coating 61. Moreover, the lowermost layer of the proximal cover glass 44 may be the chromium oxide layer 65 that is the low reflectance layer. Even in this case, the same operation and advantage as those mentioned above can be exerted.

For putting emphasis on a low reflectance, the lateral surfaces 36a and 44a of the cover glasses 36 and 44 may be polished to such an extent that the average roughness (Ra) thereof will be any of 0.1 to 1 μm and the highest roughness (PV) thereof will be any of 2 to 5 μm. The surfaces are then finished as mentioned above.

If the lateral surfaces 36a and 44a were finished like a mirror, not only light would be reflected from the surfaces but also a degree of closeness at which the layers of the coating are meeting would be lowered. If the roughness of a surface were too high, it would become hard to remove foreign matters adhering to the surface. The degree of closeness at which the layers of the coating are meeting would therefore be lowered.

Figure 7:
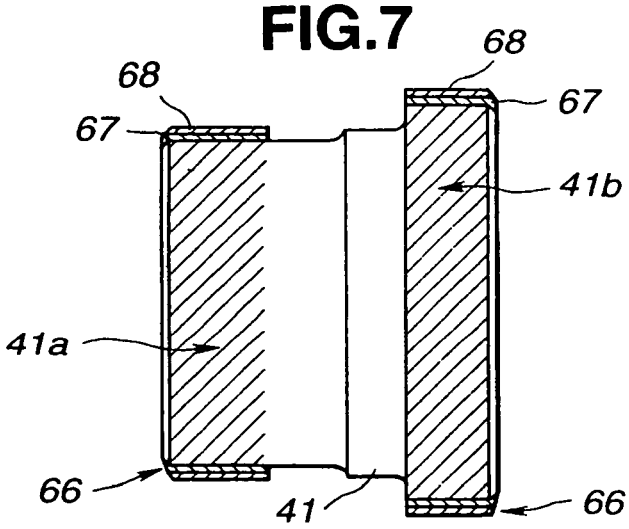

By the way, as shown in FIG. 7, a second metal coating 66 is formed on the outer surface 41a of the isolating frame 41 engaging with the distal frame 37 and the outer surface 41b of the isolating frame 41 engaging with the frame body 47.

The second metal coating 66 on the outer surfaces 41a and 41b are composed of a nickel layer 67 that is a lower layer of a metallized layer and a gold layer 68 serving as an uppermost layer. The layers are formed by performing deposition or spattering in a vacuum or by performing plating.

The outer surfaces 41a and 41b an inner surfaces are not to be finished using a conductive material. The distal frame 37 to be attached in contact with the outer surface 41a and the frame body 47 to be attached in contact with the outer surface 41b are therefore electrically isolated from each other.

Referring to FIG. 8, a description will be made of airtight joining of the frame body 47 and proximal cover glass 44.

Figure 8A:
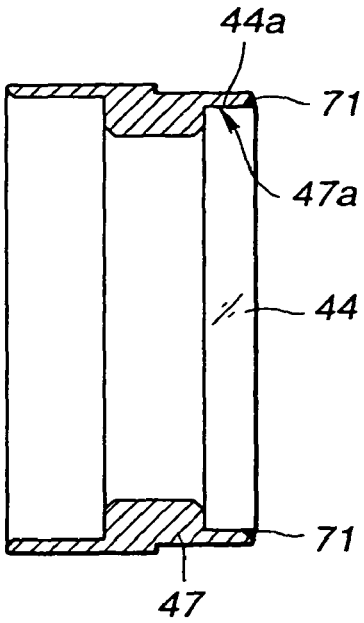
FIG. 8A is a sectional view showing a proximal cover glass hermetically united with the isolating frame.

As shown in FIG. 8A, the depth of a recess 47a in the frame body 47 in which the proximal cover glass 44 is locked is set to a value smaller than the thickness of the proximal cover glass 44. In other words, one surface of the proximal cover glass 44 juts beyond the end surface of the frame body 47 in which the recess 47a is bored.

Figure 8B:
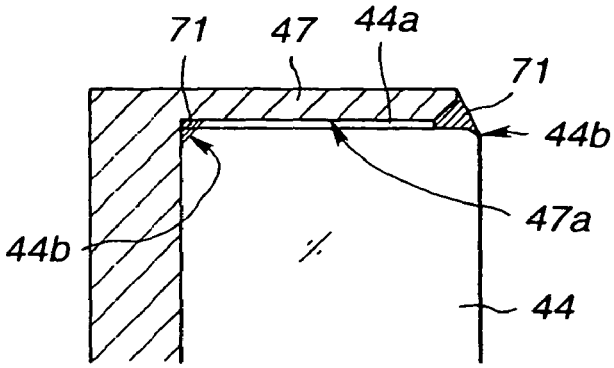
FIG. 8B is an enlarged view for explaining the airtight joint.

As shown in FIG. 8B, the lateral surface 44a of the proximal cover glass 44 and the inner circumference of the recess 47a are joined hermetically by injecting a brazing filler metal or solder into a gap between them and the edges thereof. At this time, a fillet 71 having a substantially triangular section is formed on the end surface of the frame body 47 beyond which the proximal cover glass 44 juts, and on the chamfer 44b of the proximal cover glass 44 located at a corner of the recess 47a. The fillet 71 is a lump of the brazing filler metal or solder. When the sections of the fillets 71 have a desired shape, the brazing filler metal or solder has been injected unintermittently into the gap between the lateral surface 44a of the proximal cover glass 44 and the inner circumference of the recess 47a. Thus, hermetically joining is completed. In the present embodiment, it can be visually checked whether the fillets 71 have been shaped precisely.

When flax is used for soldering or brazing, the frame body 47 and cover glass 44 must be cleaned while being joined in order to prevent corrosion of a metal.

The soldered or brazed portions do not touch a living body. Any solder or brazing filler metal can therefore be selected for use. However, preferably, an alloy of gold and tin or a gold alloy is used as a solder or brazing filler metal. The uppermost layer of the plating formed on the frame body 47 and that of the metal coating formed on the cover glass 44 are gold layers. The plating and metal coating closely meet the alloy of gold and tin or the gold alloy.

Figure 9:
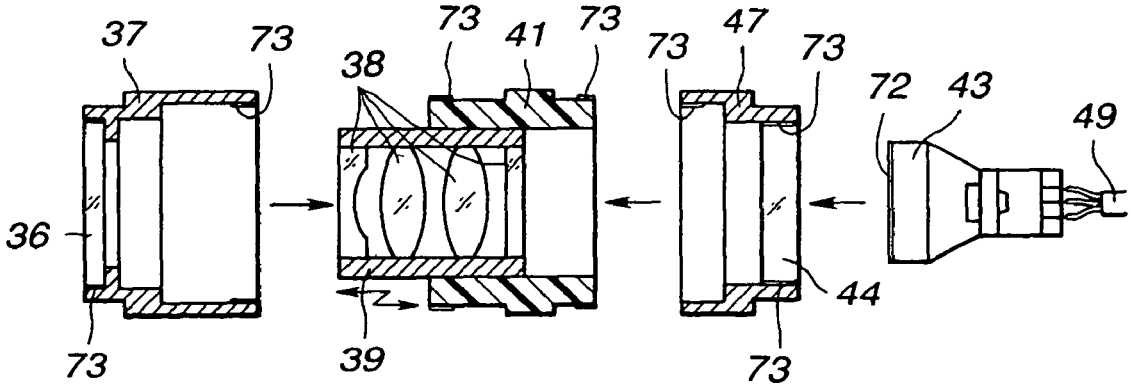
Figure 10:
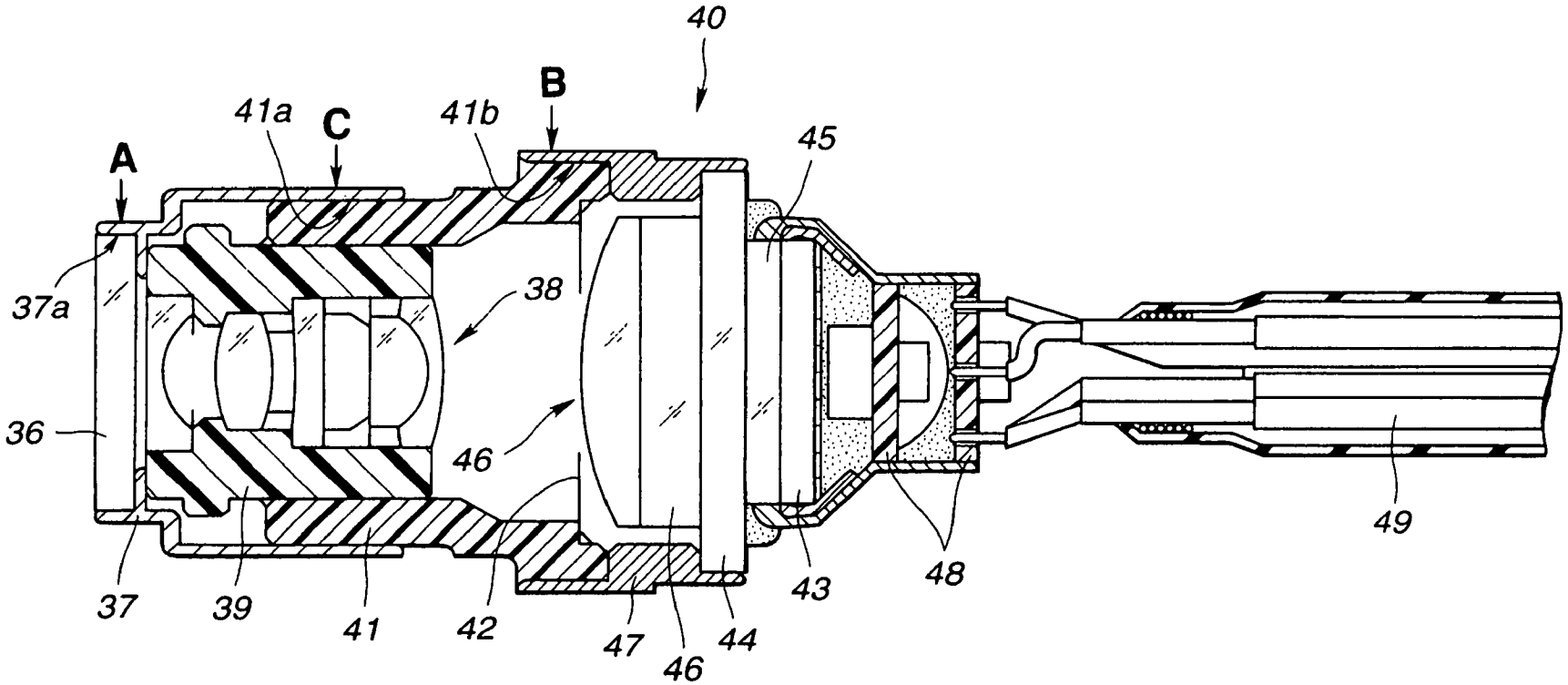

Referring to FIG. 9 and FIG. 10, a procedure of assembling the component of the imaging unit 17 will be described below.

Referring to FIG. 9, a procedure of assembling the components of an objective unit included in the imaging unit 17 will be described briefly.

The CCD 43 is bonded and fixed to the proximal end of the proximal cover glass 44, which is hermetically locked in the frame body 47, using a transparent adhesive 72 in such a manner that no air layer will be present. At this time, the center axis of the CCD 43 is aligned with that of the proximal cover glass 44. The isolating frame 41 and the frame body 47 in which the proximal cover glass 44 is locked are then joined hermetically. Thereafter, the lens frame 39 having the group of objectives 38 is inserted into the isolating frame 41. The lens frame 39 is slid along the optical axis of the group of objectives. The group of objectives 38 is focused on the CCD 43. When the group of objectives 38 has come into focus, the lens frame 39 is fixed to the isolating frame 41 using an adhesive. Thereafter, the distal frame 37 in which the distal cover glass 36 is hermetically locked and the isolating frame 41 are joined hermetically. This results in a hermetically sealed objective unit 40 shown in FIG. 10 having the whole group of objectives 38 hermetically sealed. Reference numeral 73 denotes an airtight joint realized with a solder or brazing filler metal.

Referring to FIG. 10, a description will be made of the structure of the hermetically sealed objective unit 40 in accordance with the present embodiment.

To begin with, the distal cover glass 36 having a metal coating formed on the lateral surface 36a thereof is locked in a recess 37a of the distal frame 37 that is plated. In this state, laser light is irradiated in the direction of arrow A to the whole outer circumference of the distal frame 37 in which the distal cover glass 36 is locked.

The gold layer 64 coated over the lateral surface 36a of the distal cover glass 36 and the gold layer coated over the distal frame 37 are fused with the heat of the laser light. The fused gold layers are then cooled and bonded mutually. Consequently, the outer circumference of the distal cover glass 36 and the inner circumference of the distal frame 37 are joined with no gap between them. In short, the distal cover glass 36 and distal frame 37 are joined hermetically.

A laser for irradiating laser light is preferably a YAG laser whose power is low and can be finely adjusted. Moreover, when a laser for producing laser light of a pulsating wave is used, an extent by which adjoining pulses overlap is set to 80% or higher. Thus, joining can be achieved with airtightness ensured.

Thereafter, the CCD 43 on which the substrates 48 and cable 49 are mounted is positioned on the proximal cover glass 44 and, bonded and fixed thereto. The group of lenses 46 is positioned on the proximal cover glass 44, and bonded and fixed thereto. The image input end of the CCD 43 serving as an image transmitting means and the proximal cover glass 44 are fixed to each other using a transparent adhesive.

At this time, an air layer must not be present in the layer of the adhesive. Moreover, as the transparent adhesive, an adhesive to be hardened with ultraviolet rays is used in order to reliably fix the CCD and proximal cover glass each other with the optical axes thereof aligned with each other. The portions to which the adhesive is applied lie outside the airtight region. An adhesive having the feature that it will resist high-pressure high-temperature steam given off during autoclaving so as not to be peeled off or decolorized must be selected for use. Consequently, a phenomenon causing poor image quality is prevented from occurring while involving the CCD 43 and proximal cover glass 44.

In the foregoing present embodiment, the CCD cover glass 45 is bonded to the front surface of the imaging chip included in the CCD 43. The imaging surface of the imaging chip, which is not shown, included in the CCD 43 and the CCD cover glass 45 are closely fixed to each other or hermetically sealed so that an air layer permitting invasion of steam will not be present. The front surface of the CCD cover glass 45 works substantially as the image input end of the CCD 43. However, when the CCD cover glass 45 is not included, the image input end of the imaging chip included in the CCD 43 is closely bonded directly to the proximal cover glass 44.

Thereafter, the frame body 47 is engaged with the isolating frame 41 to which the aperture stop plate 42 is bonded and fixed. Laser light is irradiated in the direction of arrow B to the whole outer circumference of the frame body 47. The gold layer 68b coated over the isolating frame 41 and the gold layer coated over the frame body 47 are fused due to the heat of the laser light. The gold layers are then cooled and bonded mutually. Thus, the outer circumference of the isolating frame 41 and the inner circumference of the frame body 47 are hermetically joined without a gap between them.

Thereafter, the lenses constituting the group of objectives 38 are assembled and fixed to the lens frame 39 using an adhesive. Thereafter, the lens frame 39 is inserted into the isolating frame 41. The position in the axial direction of the lens frame 39 is adjusted in order to bring the group of objectives 38 into focus. The lens frame 39 is then bonded and fixed to the isolating frame 41.

Thereafter, the distal frame 37 in which the distal cover glass 36 is locked is engaged with the isolating frame 41 so that it will cover the lens frame 39. Laser light is then irradiated in the direction of arrow C to the whole outer circumference of the distal frame 37. The gold layer 68 coated over the isolating frame 41 and the gold layer coated over the distal frame 37 are fused due to the heat of the laser light. The gold layers are then cooled and bonded mutually. Consequently, the outer circumference of the isolating frame 41 and the inner circumference of the distal frame 37 are joined hermetically without a gap between them.

A laser used for joining is a YAG laser whose power is low and can be finely adjusted. When components are joined using the laser, the temperature of the joint will be 1000° C. or higher. However, the heat will not adversely affect the portion of the aperture stop plate 42 to which an adhesive is applied, a joint of the CCD 43, lens frame 39, and isolating frame 41 realized with an adhesive, and the group of objectives 38. This is because laser light is irradiated locally and instantaneously.

The distal cover glass 36 and distal frame 37, the distal frame 37 and isolating frame 41, and the isolating frame 41 and frame body 47 are joined hermetically by fusing the gold layers coated over the members preliminarily using laser light. Moreover, the frame body 47 and proximal cover glass 44 are joined hermetically without a gap between them using a solder or brazing filler metal. This results in the hermetically sealed objective unit 40 that is a hermetically sealed unit sealed at a degree of sealing (hereinafter referred to as a second sealing level) at which steam will not invade into the unit during autoclaving. The hermetically sealed objective unit 40 is part of the imaging unit 18 that is one of the contents of the endoscope.

The hermetically sealed objective unit 40 is realized by unitedly joining airtight partition members using an airtight joining means. Herein, the airtight partition members are characteristic of offering a vacuum, and used to realize the distal cover glass 36, distal frame 37, isolating frame 41, frame body 47, and proximal cover glass 44. The airtight joining means enables joining without a gap between joined members. The hermetically sealed objective unit 40 is therefore so pressure-resistant and strong as to resist decompression and pressurization performed during autoclaving as well as a temperature change and not to destroy. Even if steam permeates through the armor tube made of a polymeric material and invades into the internal space during autoclaving, it can be prevented that the steam invades into the hermetically sealed objective unit 40 that is sealed at the second sealing level.

Moreover, the CCD 43 and the proximal cover glass 44 are closely joined using a transparent adhesive in such a manner that no air layer is present. By the way, the CCD 43 is located at the back end of the hermetically sealed objective unit 40, and the proximal cover glass 44 serves as an optical window and lies at the back end thereof. Along an optical path from the distal cover glass 36, which serves as an optical window bared on the distal surface of the endoscope 1, to the image input end of the CCD 43, there is no portion into which steam given off during autoclaving may invade. The steam may then condense into water. Owing to this structure, even if the solid-state imaging device is not sealed hermetically together with the objectives, nothing will hinder observation. The imaging unit can therefore be designed compactly.

The electronic parts including the solid-state imaging device are somewhat resistive to steam unlike optical members on which condensation or any other obstacle to observation occurs due to even little invading steam.

Moreover, according to the present embodiment, the first shielding frame 51 shielding the CCD 43 is mounted on the frame body 47 using an adhesive or by performing welding. The second shielding frame 52 is mounted on the first shielding frame 51 using an adhesive or by performing welding. The space created by the first shielding frame 51, CCD 43, and proximal cover glass 44 is filled with the filler 53 such as an adhesive, a sealant, or a potting material that are less permeable to steam. Moreover, the adhesive 54 is injected to the surroundings of the portion of the cable 49 lying inside the second shielding frame 52. Although the surroundings of the CCD 43 are not structured fully hermetically, at least the CCD 43 and other electronic parts are sealed at a sealing level at which they will resist steam so as not to be destroyed. Owing to the structure, the whole imaging unit 17 can resist autoclaving without the necessity of using a hermetic connector employed in the second embodiment. Besides, the imaging unit 17 can be designed compactly.

By the way, an illumination optical system is not sealed hermetically. This is because even if moisture condenses little on an illumination lens, insufficient illumination or any other functionally serious drawback will not come to light. Sealing of the illumination optical system may be of a level to be attained by securing components using an adhesive as adopted in the present embodiment.

Figure 11:
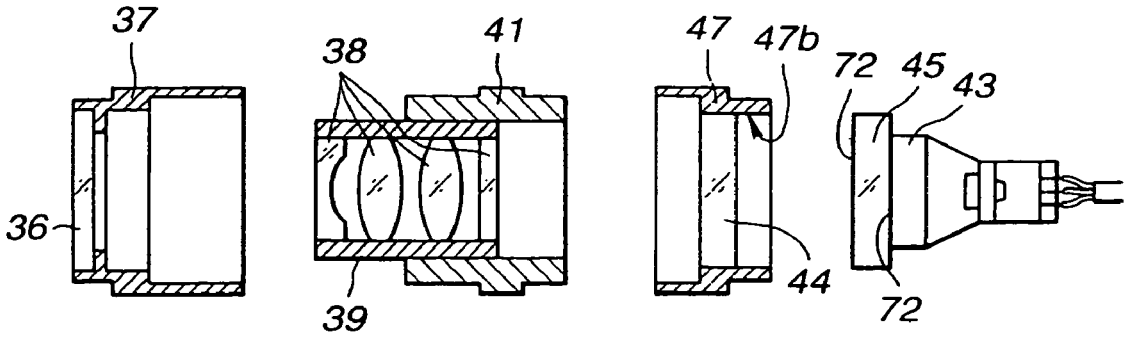
FIG. 11 is an explanatory diagram concerning a procedure of assembling lenses to produce an objective unit included in an imaging unit.

By adopting the structure shown in FIG. 11, the center axis of the CCD 43 can be readily aligned with that of the group of objectives 38.

According to the present embodiment, as illustrated, the center axis of the CCD cover glass 45 is aligned with that of the CCD 43 in advance. The CCD cover glass 45 is closely fixed to the CCD 43 by applying the transparent adhesive 72 without creating an air layer.

The proximal cover glass 44 is locked hermetically in the engagement portion 47b of the frame body 47, which is formed at the end thereof, rather than in the end portion of the frame body 47.

The CCD cover glass 45 is inserted into the engagement portion 47b of the frame body 47. The proximal cover glass 44 and CCD cover glass 45 are then closely fixed to each other by applying the transparent adhesive 72 without creating an air layer.

At this time, the center axis of the group of objectives 38 is aligned with that of the frame body 47. Owing to the structure, the center axis of the CCD 43 can be aligned readily with that of the group of objectives 38.

Figure 12:
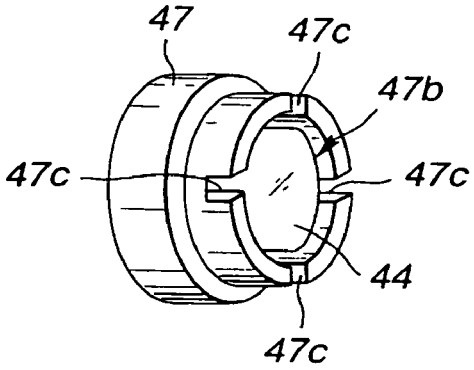
FIG. 12 is an explanatory diagram concerning notches of an engagement portion of a frame.

As shown in FIG. 12, notches 47c are formed in the engagement portion 47b of the frame body 47. When the CCD cover glass 45 is closely fixed to the proximal cover glass 44 using the adhesive 72, the excess adhesive 72 flows out of the notches 47c. Consequently, an air layer composed of babbles or the like will not be left between the CCD cover glass 45 and proximal cover glass 44.

In the structure of the present embodiment, the group of objectives 38 located in front of the image input end of the CCD 43 is placed in the hermetically sealed space. Water droplets will therefore not be produced to cloud the group of objectives 38.

Moreover, the CCD 43, CCD cover glass 45, and proximal cover glass 44 are closely fixed to one another using the transparent adhesive 72. Moisture will therefore not condense into water droplets over these members.

Figure 13:
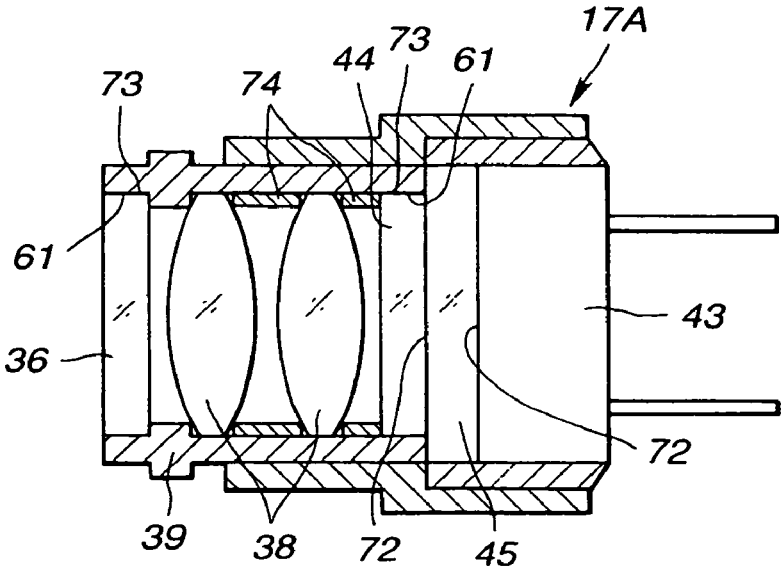
FIG. 13 is an explanatory diagram concerning an imaging unit having another structure.

Furthermore, when the group of objectives 38 is realized with a non-focus optical system, an imaging unit 17A having the structure shown in FIG. 13 should be employed.

Specifically, as illustrated, the CCD cover glass 45 is closely fixed to the image input end of the CCD 43 by applying the transparent adhesive 72 without creating an air layer. The CCD cover glass 45 is closely fixed to the proximal end surface of the proximal cover glass 44, which is hermetically locked in the lens frame 39, by applying the transparent adhesive 72 without creating an air layer.

The lens frame 39 is made of a metal or ceramic. The distal cover glass 36 made of sapphire and having the outer circumference thereof covered with the first metal coating 61 is hermetically locked in the distal part of the lens frame 39. The group of objectives 38 and spacer rings 74 are placed in the space hermetically sealed by the lens frame 39, distal cover glass 36, and proximal cover glass 44.

In the present embodiment, the group of objectives 38 is located at a position, at which it is focused on the CCD 43, by means of the spacer rings 74. This obviates the necessity of bringing the group of objectives into focus during assembling. Consequently, it becomes unnecessary to hermetically join units with the CCD included in one of the units by performing soldering or brazing. Assembling efficiency therefore improves. The other operations and advantages are identical to those exerted by the aforesaid embodiment.

Raw materials to be made into the airtight partition members constituting the hermetically sealed objective unit 40 and hermetically sealing it, such as, a metal, a ceramic, a glass, and sapphire are highly heat-resistant and pressure-resistant to resist decompression or pressurization performed during autoclaving and not to be destroyed. Moreover, the raw materials themselves are characteristic of offering a vacuum (when the volume of a space in a specimen is any of 0.1 to 0.4 $cm^3$, a syntype leakage detected by a helium leakage detector stipulated in the JIS Z2331 is $1\times10^{-9}$ $Pa\cdot m^3/s$ or less). Besides, the raw materials can be joined hermetically.

The raw materials that can be joined hermetically are heat-resistant raw materials that are resistive to a temperature rise occurring when the raw materials are joined using an airtight joining means described below.

By contrast, polymeric materials including general resins and rubbers cannot clear the conditions for airtight partition members. The raw materials to be made into the airtight partition members are therefore limited to raw materials whose main components are a metal, a ceramic, a glass, or a crystalline material. Any preferable raw material is selected from among these raw materials.

As for the metal, various raw materials can be used. For example, stainless steel or covar can be used.

Moreover, in the present embodiment, ceramic and glass are distinguished from each other as if they were different raw materials. However, ceramic is a generic name of non-metallic inorganic materials produced through steps of molding and baking and others. Therefore a broad sense, glasses are included in ceramics. Many ceramics meet the conditions for airtight partition members. When a metal cannot be adopted as a material of airtight partition members for the insulation-related and optical reasons, another ceramics is adopted.

However, some ceramics are less characteristic of offering a vacuum, are likely to crack due to heating performed for airtight joining, or may deteriorate terribly due to steam. A ceramic must therefore be selected after profound thought.

Preferably, a fine ceramic having an insulation property and being susceptible to a vacuum, such as, aluminum nitride, sialon, alumina, silicon oxide, or silicon carbide should be used to produce insulating members.

Moreover, many multi-component glasses used to produce optical members in general are deteriorated with steam. An optical member used as an airtight partition member, that is, an optical window should be made of a crystalline material that is transparent or has the property of transmitting light, or a multi-component glass that is resistive to high-pressure high-temperature steam. Sapphire is a monocrystal of $Al_2O_3$ and classified into transparent crystalline materials. Sapphire is therefore a typical optical material capable of clearing the conditions for airtight partition members. Another transparent crystalline material is quartz.

In the present embodiment, a means for fusing a gold plate by utilizing heat stemming from irradiation of laser light is adopted as an airtight joining means. Otherwise, soldering, brazing, or brazing and soldering may be adopted as an airtight joining means. The present invention is not limited to these methods. Alternatively, various kinds of welding may be adopted as a joining means.

Various kinds of welding include fusion welding represented by laser welding or electron-beam welding, pressure welding represented by resistance welding, and brazing or soldering. When any of these methods is adopted as a joining means, airtight joining can be achieved. For example, laser welding may be adopted to join two metallic parts serving as airtight partition members. The two metallic parts are fused and united. The joint of the two metallic parts consists of the airtight partition members alone. Reliable airtightness can be ensured.

When brazing and soldering is adopted, the joint of airtight partition members is infiltrated with a metal. Airtightness can therefore be ensured. Brazing filler metals include a gold alloy, a silver alloy, a nickel alloy, a copper alloy, and other various alloys. However, the gold alloy, nickel alloy, or any other alloys that hardly corrode should be selected in consideration of the resistivity to corrosion. Moreover, solders include, aside from a generally adopted alloy of lead and tin, a silver alloy, a copper alloy, and an alloy of gold and tin. Solders that hardly corrode, such as, the highly corrosion-resistant alloy of gold and tin should be selected.

Moreover, aside from metal welding, joining using a molten glass is also a joining means enabling airtight joining. This joining means can be adopted naturally. The molten glasses to be injected to a gap between members to be joined hermetically include a low fusion point powdered glass. A molten glass is heated and fused, and then injected into a joint of airtight partition members in order to attain airtightness.

The low fusion point powered glass falls into a type to be shaped like a plate glass and a crystallized type. Ceramics other than glasses are baked to become jointing materials enabling airtight joining. As a joining means for realizing a joint whose major component is a metal, ceramic, glass, or crystalline material, any ceramic can be adopted. The ceramic works as an airtight joining means.

When any of the aforesaid airtight joining means is used to join members, the temperature of a joint of the members often rises considerably. For example, when soldering that is a typical metal welding method is adopted, the temperature rises to 200° C. to 400° C. In the case of brazing, the temperature rises to 700° C. to 1000° C. Furthermore, in the case of laser welding, the temperature rises to the fusion temperature of a metal. Specifically, when stainless steel is used, the temperature rises to about 1400° C. In the case of a low fusion point glass generally adopted as a molten glass for airtight joining, the fusion point thereof is 300° C. to 600° C.

Operations to be exerted by the endoscope having the foregoing structures will be described below.

After the endoscope is used, even if the endoscope can be autoclaved, the endoscope is cleaned without fail. For the cleaning, at least the waterproof cap 15 is attached in order to prevent invasion of a fluid during cleaning under running water or immersion in a fluid agent. The whole housing of the endoscope is thus sealed in a watertight manner at the first sealing level. Consequently, it is prevented that a fluid invades into the interior of the endoscope during cleaning of the endoscope, and that the internal members of the endoscope deteriorate.

Thereafter, when cleaning is completed, the waterproof cap 15 is detached and the non-return valve cap 20 is attached. The endoscope 1 is then sterilized using a pre-vacuum type autoclave.

At the pre-vacuum step, the internal space of the endoscope 1 is deaerated externally through the non-return valve cap 20.

This causes a difference in pressure between the interior and exterior of the hermetically sealed objective unit 40 that is hermetically sealed at the second sealing level. However, it will not take place that the armor tube 35 of the bendable part 9 serving as an integral part of the endoscope housing dilates to burst. Moreover, the hermetically sealed objective unit 40 is composed of airtight partition members or realized by hermetically joining the airtight partition members. It will therefore not take place that the hermetically sealed objective unit 40 is destroyed due to the pressure difference.

At the subsequent sterilization step, the non-return valve cap 20 is attached. High-pressure high-temperature steam will therefore not actively invade into the internal endoscope space. However, high-pressure high-temperature steam permeates through the armor tube 35 and others, which are made of a polymeric material and constitute the endoscope housing, and invades gradually into the internal endoscope space. However, the hermetically sealed objective unit 40 is composed of airtight partition members or realized by hermetically joining the airtight partition members. Steam will therefore not invade into the hermetically sealed objective unit 40. Moreover, the endoscope 1 is heated up to any of temperatures ranging from 115 to 140° C. However, it will not take place that the hermetically sealed objective unit 40 is destroyed due to the temperature change.

The drying step succeeds the sterilization step. The same pressure difference as that occurring at the pre-vacuum step occurs between the interior and exterior of the hermetically sealed objective unit 40. At this time, it will not take place that the hermetically sealed objective unit 40 is destroyed due to the pressure difference, temperature change, or any other adverse effect. Furthermore, steam will not invade into the hermetically sealed objective unit 40.

After autoclaving is completed, the pressure in the internal endoscope space becomes lower than the atmospheric pressure. The armor tube 35 of the bendable part 9 therefore sticks to the internal structure.

If the bendable part were bent in this state, the armor tube 35 would be damaged. However, before the endoscope is put to use, the camera connector 7 must be attached to the CCU. In other words, the non-return valve cap 20 is detached from the camera connector 7 without fail. Therefore, atmospheric air flows into the internal space through the vent 14 of the camera connector 7. This eliminates the pressure difference between the interior and exterior of the hermetically sealed objective unit 40 and that between the internal endoscope space and the exterior. Consequently, the armor tube 35 is unsticked from the internal structure. The armor tube 35 will therefore not be damaged during bending.

The present embodiment is concerned with an endoscope for medical studies to be autoclaved. The structure in accordance with the present invention may be adapted to an endoscope to be sterilized with steam, an endoscope to be immersed in a fluid agent for a long time, an endoscope having a possibility that steam may invade into the interior thereof, and an endoscope to be used in a highly humid environment, for example, an endoscope for industrial use.

Moreover, the present embodiment is concerned with an endoscope whose insertion unit 2 has the bendable part 9. Alternatively, the structure in accordance with the present invention may be adapted to an endoscope having a rigid insertion unit part of which is formed as the bendable part 9, or an endoscope whose insertion unit is made soft and has no bendable part.

The present embodiment provides the advantages described below.

Even when a bendable endoscope having a housing member thereof made of a polymeric material is autoclaved, an armor tube sheathing a bendable part will not burst.

Even when the endoscope is autoclaved, steam will not permeate through airtight partition members outlining a hermetically sealed objective unit or joints at which the airtight partition members are hermetically joined, and will therefore not invade into the interior of the endoscope. Consequently, it is prevented that the quality of a view is impaired due to condensation on a lens.

Even when the endoscope is autoclaved, neither the airtight partition members outlining the hermetically sealed objective unit nor joints at which the airtight partition members are hermetically joined will be destroyed. It will therefore not take place that steam invades into the interior due to destruction. Needless to say, it will not take place that the quality of a view is impaired due to condensation on a lens.

When the endoscope is autoclaved, steam is prevented from actively invading into the internal endoscope space owing to a non-return valve cap. Deterioration of the internal members of the endoscope will therefore be alleviated. Moreover, after autoclaving is completed, before the endoscope is used, the non-return valve cap is detached from a camera connector. It will therefore not take place that the endoscope is put to use with the pressure in the internal space thereof left lower than the outside air pressure. This eliminates the possibility that the armor tube of a bendable part is flawed when used while being stuck to the internal structure.

The hermetically sealed objective unit is placed in close contact with the image input end of a solid-state imaging device. It will not take place that a field of view is narrowed due to autoclaving. Moreover, an imaging unit can be designed compactly. The rigid part of the imaging unit can be placed within a distal rigid length covering the bendable part of the bendable endoscope. Besides, the distal rigid length can be shortened.

The imaging unit has the objective unit hermetically sealed. The portion enclosing the solid-state imaging device is sealed using a joining means, for example an adhesive. Thus when the endoscope is autoclaved, the solid-state imaging device will not be destroyed and the quality of a view will not be impaired. Moreover, the imaging unit can be designed compactly. Despite the bendable endoscope, the rigid part of the imaging unit is resistive to autoclaving and can therefore be placed within the distal rigid length covering the bendable part. Moreover, it is prevented that the distal rigid length extends.

Airtightness described in relation to the present invention shall be referred to a state in which a syntype leakage (the volume of the internal space of a specimen falls within the range of 0.1 to 0.4 $cm^3$) detected by a helium leakage detector stipulated in the JIS Z2331 is $1\times10^{-9}\cdot m^3/s$ or less.

When the syntype leakage exceeds $1\times10^{-9}\cdot m^3/s$, steam may invade during autoclaving. Otherwise, when autoclaving is repeated, steam may accumulate to condense on a lens or cloud it. Consequently, the lens, a coating covering the surface of the lens, or an adhesive may deteriorate to cause a drawback such as the impaired quality of a view.

Table 1 lists different syntype leakages and whether or not steam invades in association with different joining methods.

An airtight structure realized by performing welding, or in short, the airtight structure of the hermetically sealed objective unit 40 described in relation to the above embodiment is apparently different from a watertight structure realized using a typical O ring or adhesive in terms of the syntype leakage.

TABLE 1

| Joining method | Syntype leakage ($Pa \cdot m^3/s$) | Invasion of steam |
|---|---|---|
| Welding | $0.6 \times 10^{-10}$ to $1 \times 10^{-9}$ | Not observed |
| Sealing with O ring (fluorine-contained rubber) | $1 \times 10^{-9}$ to $1 \times 10^{-8}$ | Observed |
| Sealing with O ring (silicon rubber) | $5 \times 10^{-8}$ to $5 \times 10^{-7}$ | Observed |
| Fixation with epoxy resin adhesive | $5 \times 10^{-10}$ to $1 \times 10^{-7}$ | Observed |

The data indicating whether steam invades after autoclaving demonstrates that compared with when welding including brazing and welding, and fusion welding is adopted, when an adhesive or sealer made from a polymeric material is adopted, steam invades through an adhesive-applied portion or sealer member. This becomes more obvious after autoclaving is repeated.

Figure 14:
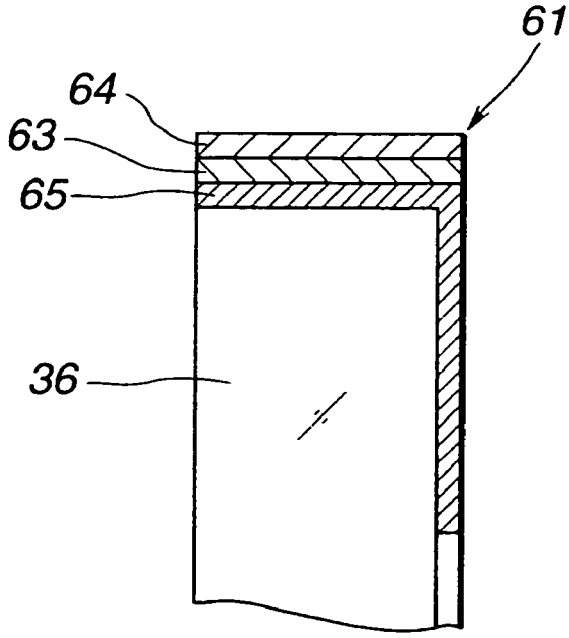
FIG. 14 is a sectional view for explaining a beam narrowing mask created on the proximal surface of the distal cover glass.
Figure 15:
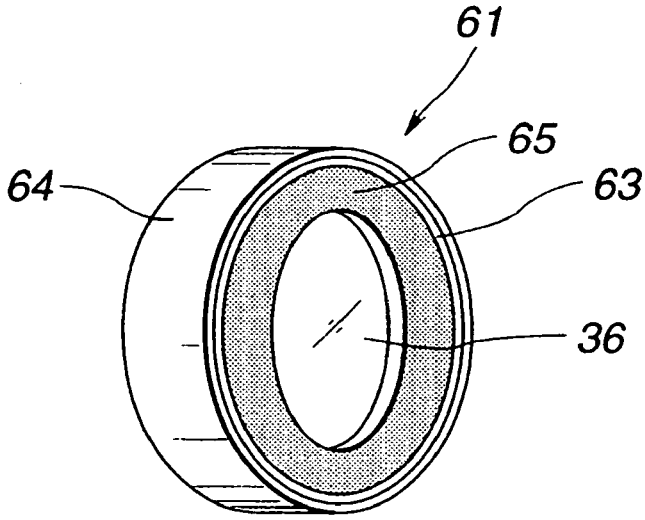
FIG. 15 is a perspective view of the distal cover glass for explaining the beam narrowing mask created on the proximal surface of the distal cover glass.

Furthermore, as shown in FIG. 14 and FIG. 15, the chromium oxide ($Cr_2O_3$) plate layer 65 may be formed not only on the outer circumference of the distal cover glass 36 but also on a doughnut-shaped portion of the proximal end surface thereof. The plate layer 65 is the low reflectance layer of the first metal coating 61 formed on the distal cover glass 36. In this case, the chromium oxide plate layer 65 on the doughnut-shaped portion can function as a mask for narrowing a beam.

Thus, the low reflectance layer intended to prevent flare is thus assigned to the role of the mask for narrowing a beam. This obviates the necessity of separately preparing a mask member for narrowing a beam, thus contributing to a reduction in the number of parts. Eventually, the cost of the endoscope can be minimized.

Figure 16:
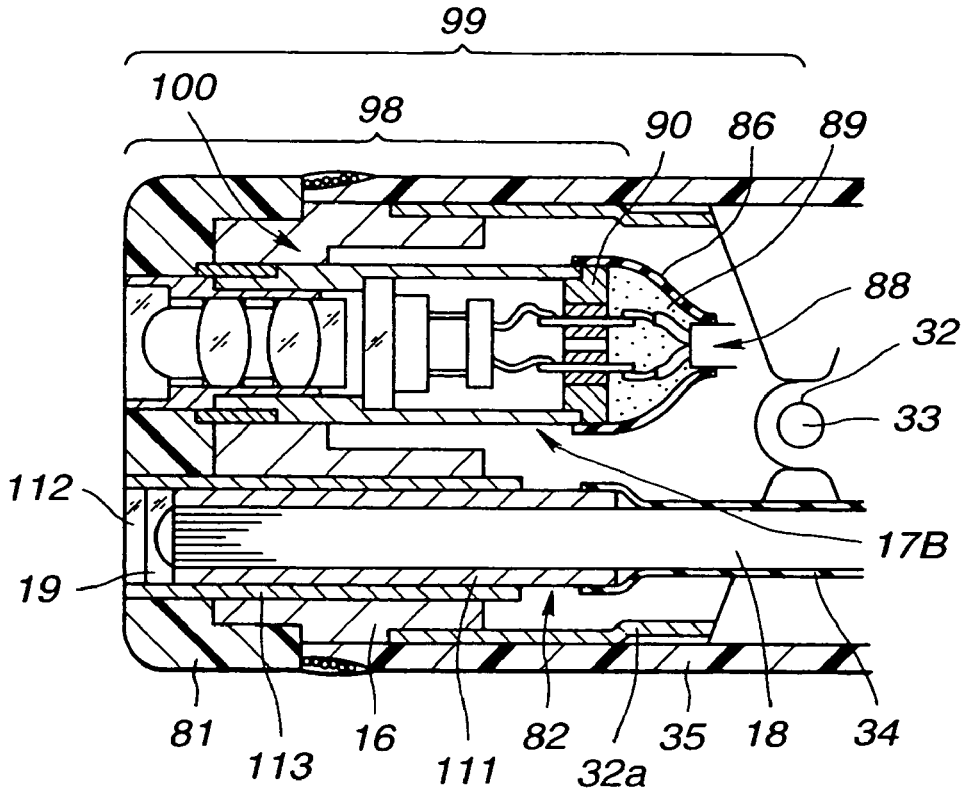
FIG. 16 and FIG. 17 relate to a second embodiment of the present invention.
Figure 17:
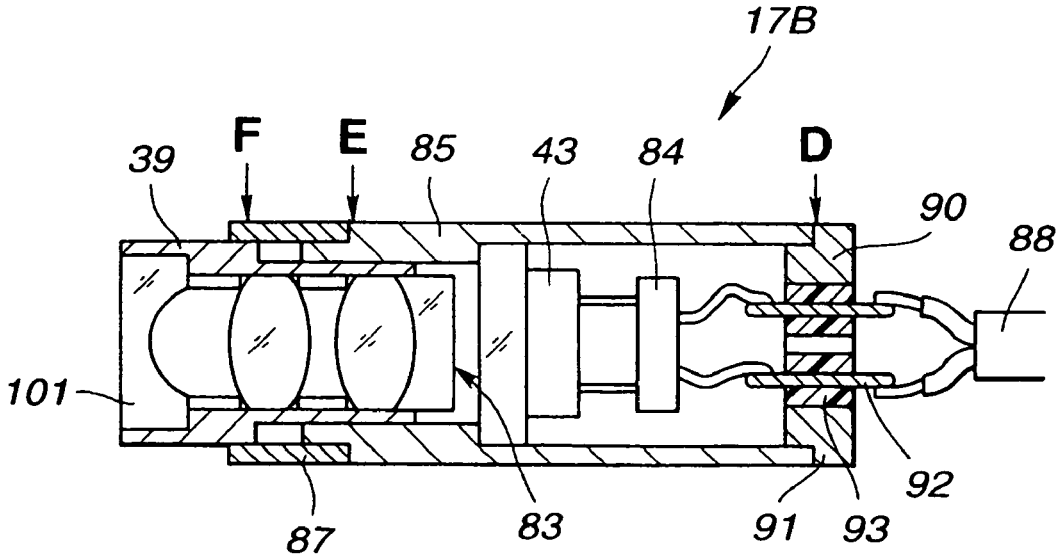

Referring to FIG. 16 and FIG. 17, the second embodiment of the present invention will be described below.

The overall configuration of the present embodiment is substantially identical to that of the first embodiment shown in FIG. 1. The same reference numerals will be assigned to identical components and only the description of the components different from those of the first embodiment will be described below.

As shown in FIG. 16, the distal part 8 of the insertion unit 2 of the endoscope 1 in accordance with the present embodiment consists mainly of the metallic distal body 16, a distal cover 81, an imaging unit 17B, and a light guide unit 82. The imaging unit 17B is inserted into through holes bored in the distal body 16 and distal cover 81 and locked therein, and serves as an observing means and image transmitting means. The light guide unit 82 serves as an illuminating means.

The distal cover 81 fills the role of an insulator, and is made of a plastic that has an insulation property, and is heat-resistant and waterproof, such as, polyphenylene sulphite, polyphenyl sulfone, polyether ether ketone, or a ceramic.

The first bending piece 32a is located at the foremost end of the plurality of bending pieces constituting the bendable part 9, and fixed at the proximal end of the distal body 16. The bending pieces 32 are concatenated using the rivets 33 so that they can pivot freely. The distal part of the armor tube 35 is fixed to the outer circumference of the distal body 16 in a watertight manner. The armor tube 35 is made from a soft polymeric material such as a fluorine-contained rubber, and sheathing the outer circumferences of the bending pieces 32 constituting the bendable part 9.

As shown in FIG. 17, the imaging unit 17B in accordance with the present embodiment consists mainly of a group of objectives 83, the CCD 43, a substrate 84, the lens frame 39, a CCD frame 85, a hermetic connector 90, an airtightness retaining pipe 87, and a CCD cable 88. The group of objectives 83 forms an object image. The CCD 43 has the formed object image projected thereon. Capacitors, ICs, and other electronic parts for processing an electric signal produced by the CCD 43 are mounted on the substrate 84. The lens frame 39 made of a metal serves as an airtight partition member for holding the group of objectives 38. The CCD frame 85 made of a metal serves as an airtight partition member for holding the CCD 43, and is engaged with the proximal part of the lens frame 39. The hermetic connector 90 is attached to the proximal end of the CCD frame 85. The airtightness retaining pipe 87 made of a metal serves as an airtight partition member, and is placed over the lens frame 39 and CCD frame 85 and engaged with them. The CCD cable 88 is coupled to the hermetic connector 90.

The hermetic connector 90 has metallic contact pins 92 passed through holes bored in a metallic connector body 91 serving as an airtight partition member. An insulating and airtight sealing member 93 made from a molten glass and serving as one of airtight joining means is poured into the through holes. The contact pins 92 are thus isolated from the connector body 91. Since the through holes are filled with the molten glass, there is no gap between each contact pin 92 and the wall of a through hole. Thus, the contact pins 92 are hermetically locked in the connector body 91.

As shown in FIG. 16, the hermetic connector 90 and CCD cable 88 are sheathed with a thermo-contractile tube 86. The interior of the thermo-contractile tube 86 is filled with a filler 89 that is an epoxy adhesive, ceramic adhesive, or silicon adhesive. Joints of the contact pins 92 and the signal lines contained in the CCD cable 88, that is, the portions thereof which are joined using a solder or the like and having a metal thereof bared are covered by the filler 89. The joints are thus prevented from corroding due to steam. A range 98 corresponding to the length of the distal rigid part of the imaging unit 17 B falls within a distal rigid length indicated as a range 99 distal to the rivet 33 located at the foremost end of the bending part 9.

As shown in FIG. 17, a first lens 101 lies at the foremost end of the group of objectives 83, and serves as an optical window forming the distal end surface of the endoscope 1. The first lens 101 is made of sapphire or a glass resistive to high-pressure high-temperature steam. Metal coating described in relation to the first embodiment is performed on the lateral surface and chamfer of the first lens 101. The first lens 101 is hermetically locked in the metallic lens frame 39 by performing laser welding that is an airtight joining means described in relation to the first embodiment.

The CCD frame 85 and hermetic connector 90 are hermetically joined by performing welding. For the welding, laser light is irradiated in the direction of arrow D to the whole circumference of a junction at which the CCD frame 85 meets the hermetic connector 90. The CCD frame 85 and hermetic connector 90 are thus fused and united with each other.

Furthermore, before the CCD frame 85 and hermetic connector 90 are joined, the lens frame 39 having the group of objectives 83 locked therein is engaged with the CCD frame 85. The lens frame 39 is moved in the axial directions in order to bring the group of objectives 83 into focus. When the group of objectives 83 comes into focus, the lens frame 39 is fixed to the CCD frame 85 using an adhesive.

Thereafter, the airtightness retaining pipe 87 is placed over the lens frame 39 and CCD frame 85. In this state, laser light is irradiated in the direction of arrow E to the whole circumference of the airtightness retaining pipe 87. Thus, the meeting portions of the airtightness retaining pipe 87 and CCD frame 85 are welded, and the airtightness retaining pipe 87 and CCD frame 85 are joined hermetically. Laser light is then irradiated in the direction of arrow F to the whole circumference of the airtightness retaining pipe 87. Thus, the meeting portions of the airtightness retaining pipe 87 and lens frame 89 are welded, and the airtightness retaining pipe 87 and lens frame 89 are hermetically joined. This results in a hermetically sealed imaging unit body 100 that is sealed at the same second sealing level as the hermetically sealed objective unit 40 in the first embodiment.

A laser employed is, similarly to that in the first embodiment, a YAG laser whose power is low and can be finely adjusted. Moreover, when laser light of a pulsating wave is irradiated, a degree by which adjoining pulses overlap is set to 80% or higher. Consequently, reliable airtightness can be ensured.

The light guide unit 82 shown in FIG. 16 consists of the light guide fiber bundle 18, a first light guide fiber frame 111, the illumination lens 19, an illumination cover member 112, an illumination lens frame 113, and a light guide fiber casing tube 114. The light guide fiber bundle 18 is formed as an optical fiber bundle made by bundling fibers or a plurality of optical fibers each composed of a core and cladding. The first light guide fiber frame 111 made of a metal serves as an airtight partition member having the light guide fiber bundle 18 incorporated therein. The illumination lens 19 is located on the distal surface of the light guide fiber bundle 18, and spreads an angle of illumination. The illumination cover member 112 made of sapphire serves as an airtight partition member located on the distal surface of the illumination lens 19. The illumination lens frame 113 made of a metal serves as an airtight partition member having the illumination cover member 112 and others incorporated therein. The light guide fiber casing tube 114 has one end thereof located at the proximal end of the illumination lens frame 113, and encases the light guide fiber bundle 18.

A molten glass that is one of airtight joining means is infiltrated into the distal part of the light guide fiber bundle 18 inserted in the first light guide fiber frame 111, whereby the fibers of the light guide fiber bundle 18 are joined hermetically. In other words, a molten glass (not shown) is infiltrated unintermittently into the fibers constituting the light guide fiber bundle 18. The molten glass should be a paste-type low fusion point powered glass in which an organic binder is mixed. The fusion point of the low fusion point powered glass is lower than that of a fiber. The low fusion point powered glass will not be re-fused due to heat of illumination light. The fusion temperature of the low fusion point powered glass falls within the range of 300 to 600° C. Moreover, the low fusion point powered glass can be handled easily during assembling.

Before the paste-type low fusion point powered glass is used to join the fibers of the fiber bundle, first, the fiber bundle infiltrated with the low fusion point powered glass is inserted into the first light guide fiber frame 111. The portion of the fiber bundle infiltrated with the powered glass is heated at any of temperatures ranging from 300 to 600° C., whereby the organic binder is dispersed. When the low fusion point powered glass is fused, the portion infiltrated with the low fusion point powered glass is then cooled.

Thus, the molten glass is hermetically infiltrated into the fibers. Moreover, the outer circumference of the end portion of the light guide fiber bundle 18 having the molten glass infiltrated into the fibers thereof and the inner circumference of the light guide fiber frame 111 are joined hermetically owing to the molten glass.

The molten glass fills the role of an airtightness retaining filler to be infiltrated into the fibers, and the role of an airtight joining means for hermetically joining the light guide fiber bundle 18 and first light guide fiber frame 111.

The same metal coating as that employed in the first embodiment is performed on the outer circumference of the illumination cover member 112. The illumination cover member 112 and illumination lens frame 113 are hermetically joined by the same airtight joining means as that employed in the first embodiment.

The structure of the light guide unit 82 will be described more particularly.

To begin with, the illumination lens 19 is put in the illumination lens frame 113 hermetically united with the illumination cover member 112. Thereafter, the light guide fiber frame 111 hermetically united with the end of the light guide fiber bundle 18 owing to the molten glass is put in the illumination lens frame 113. Laser welding is then performed in order to hermetically join the illumination lens frame 113 and light guide fiber frame 111.

Consequently, the portion enclosed with the illumination cover member 112, illumination lens frame 113, first light guide fiber frame 111, and end of the light guide fiber bundle 18 is hermetically sealed in the same manner as the hermetically sealed imaging unit body 100.

Owing to the foregoing structure, steam is prevented from permeating through the light guide fiber casing tube 114 and invading into the illumination lens 19 through the fibers and the gap between the light guide fiber bundle 18 and first light guide fiber frame 111.

Owing to the foregoing structure, the illumination lens 19 is placed in the fully hermetically sealed space. An airtight partition member need not be used as the illumination lens 19, but a generally employed multi-component glass that can be machined quite readily can be adopted.

Furthermore, the illumination lens 19 may be made of sapphire or any other optical material resistive to high-pressure high-temperature steam. The illumination lens 19 and first light guide fiber frame 111 may then be hermetically joined directly. According to this structure, the illumination cover member 112 can be excluded. In either structure, moisture will not condense on the inner surface of the illumination lens 19. Eventually, insufficient illumination will not arise.

Figure 18:
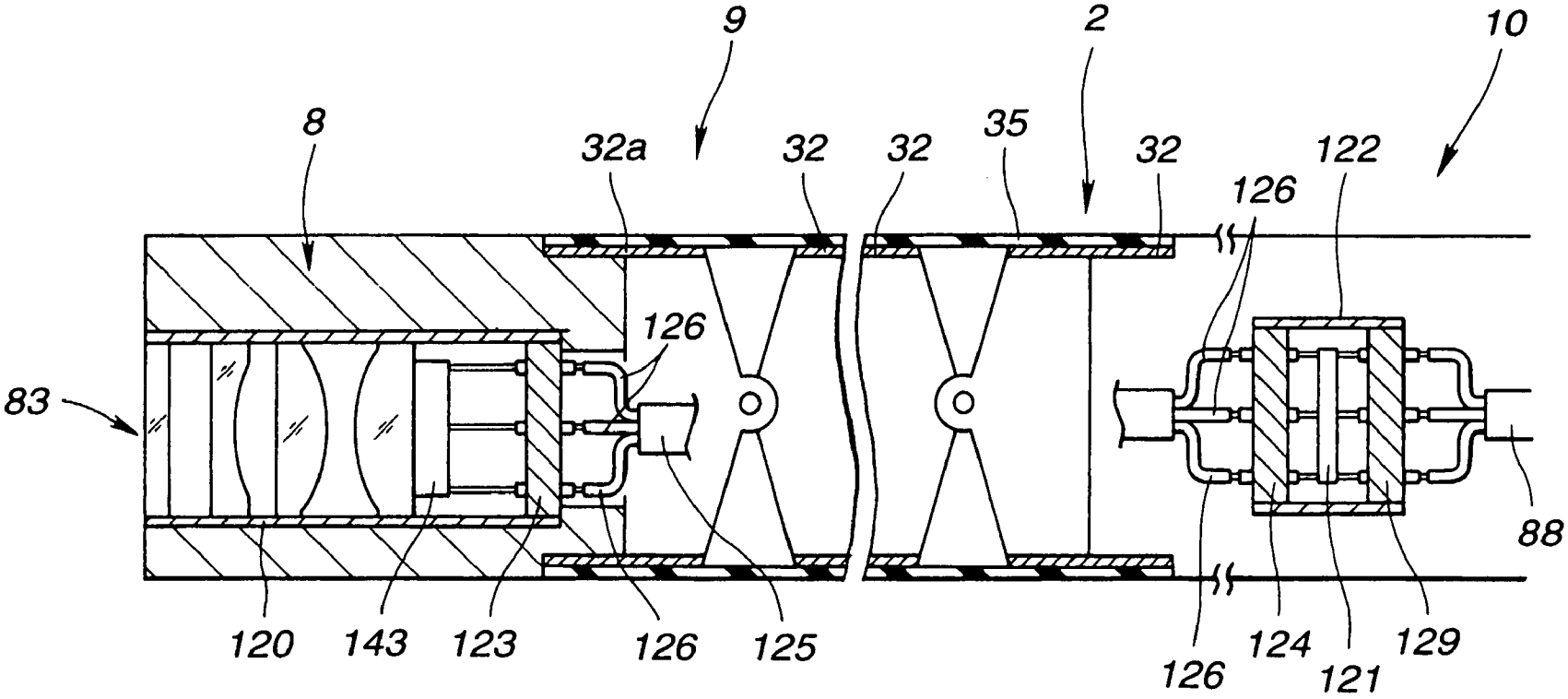
FIG. 18 shows the electronic endoscope having a device frame and HIC frame linked by a relay cable.

In the endoscope of the present embodiment, as another example, as shown in FIG. 18, a device frame 120 accommodating the group of objectives 83 and CCD 43 may be included in the distal rigid part. An HIC frame 122 accommodating a hybrid integrated circuit (hereinafter, an HIC) 121 may be placed in the flexible tube 10 located behind the bendable part 9. In this case, a connector 123 locked in the device frame 120 and a distal connector 124 locked in the HIC frame 122 are electrically linked by a plurality of signal cables 126 contained in a relay cable 125 lying through the bendable part 9.

Figure 19:
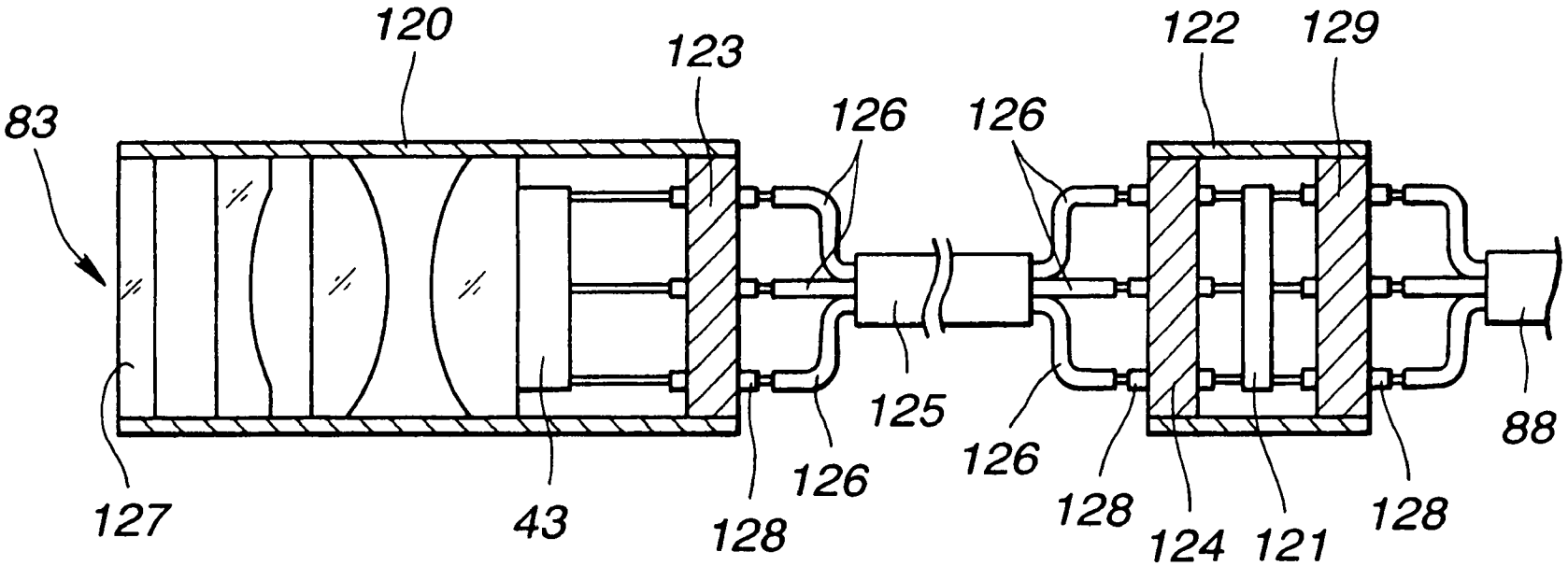
FIG. 19 is an explanatory diagram for detailing the device frame, HIC frame, and relay cable.

As shown in FIG. 19, a distal cover glass 127 made of sapphire is, like the one in the aforesaid embodiment, hermetically locked in the distal part of the device frame 120. The connector 123 is hermetically locked in the proximal part thereof by performing metal welding such as fusion welding, brazing or pressure welding. Thus, the lens unit 83 and CCD 43 are placed in the hermetically sealed internal space of the device frame 120.

Connection pins 128 like the aforesaid ones are hermetically implanted in the connector 123 using a molten glass. The distal ends of the connection pins 128 are electrically connected to the CCD 43, while the proximal ends thereof are electrically coupled to the signal cables 126 contained in the relay cable 125.

By the way, the distal connector 124 and proximal connector 129 are locked in the distal part of the HIC frame 122 and the proximal part thereof respectively. The outer circumferences of the connectors 124 and 129 and the inner circumference of the HIC frame 122 are hermetically joined by performing metal welding such as fusion welding, brazing and welding, or pressure welding. Thus, the HIC 121 is placed in the hermetically sealed internal space of the HIC frame 122.

The bar-like connection pins 128 are hermetically implanted in the connectors 124 and 129 using a molten glass in the same manner as that mentioned above. The signal cables 126 bared at the proximal end of the relay cable 125 are electrically spliced to the distal ends of the connection pins 128 implanted in the distal connector 124. The proximal ends of the connection pins 128 are electrically coupled to one surface of the HIC 121.

Moreover, the distal ends of the connection pins 128 implanted in the proximal connector 129 are electrically coupled to the other end surface of the HIC 121. The signal lines contained in the CCD cable 88 extending to the connector unit 5 are spliced to the proximal ends of the connection pins 128.

As mentioned above, the HIC 121 is not placed in the distal rigid part but placed in the flexible tube 10. This leads to the shortened distal rigid part.

Moreover, the CCD 43 placed in the distal rigid part is electrically connected to the HIC 121 placed in the flexible tube over the relay cable. The ratio at which the contents of the distal rigid part and those of the bendable part occupy the internal spaces of the distal rigid part and bendable part can be set to the same values as those set for a conventional endoscope.

Figure 20:
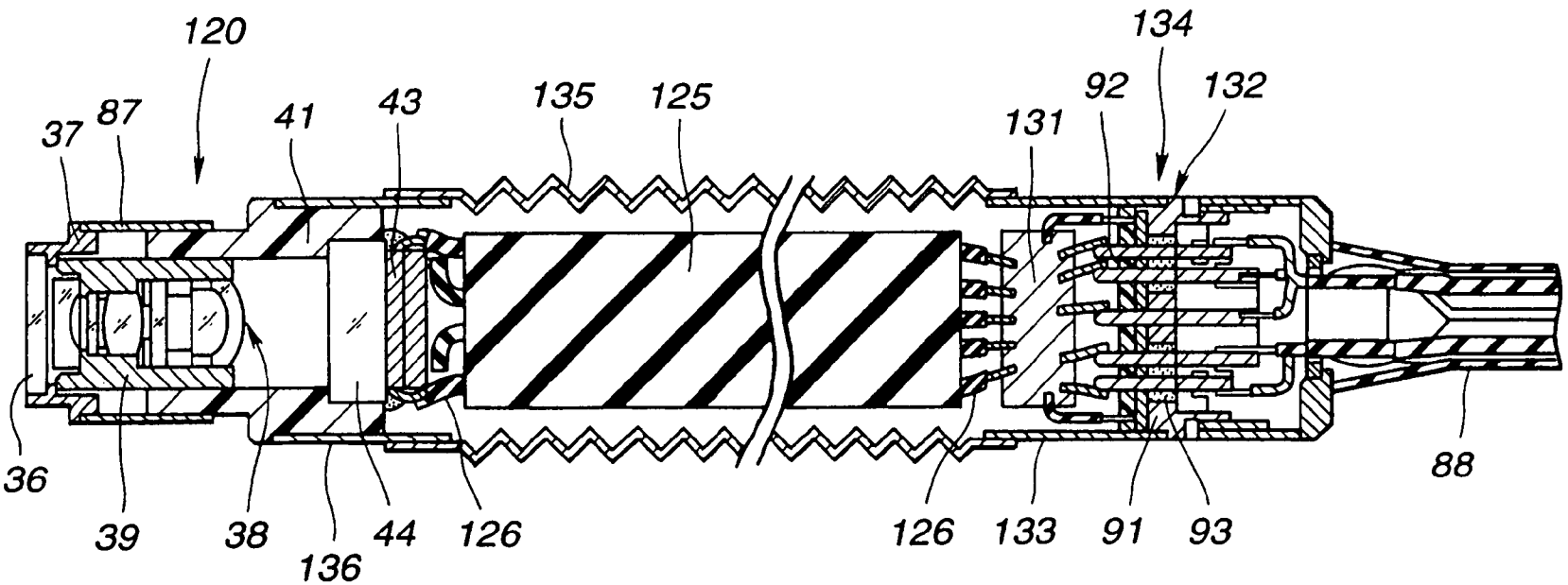
FIG. 20 shows an electronic endoscope having a device frame and substrate frame linked by a relay cable.

For example, as shown in FIG. 20, the device frame 120 placed in an airtight space and a substrate frame 134 having a substrate 131 and hermetic connector 132 placed in a metallic sleeve 133 are separated from each other, and electrically linked by the relay cable 125. The airtight space is defined by the lens frame 39 accommodating the group of objectives 38, the distal frame 37 having the distal cover glass 36 locked therein, the isolating frame 41 having the proximal cover glass 44 locked therein, and the airtightness retaining pipe 87 hermetically united with the isolating frame 41 and distal frame 37. At this time, the relay cable 125 is sheathed with a soft tube 135 that is pleated to be bendable and foiled with, for example, stainless steel or aluminum. The distal part of the soft tube 135 is overlaid the proximal part of a metallic connection frame 136 joining the isolating frame 41. The proximal part of the soft tube 135 is overlaid the distal part of the sleeve 133. Thus, the soft tube 135 and the connection frame 136 and sleeve 133 are hermetically joined by performing metal welding or the like.

Consequently, the signal cables 126 lying through the relay cable 125 and the contacts of the signal cables 126 and connection pins 92 will not be exposed to high-pressure high-temperature steam.

Now, the structure of the light guide connector 6 will be described below.

Figure 21:
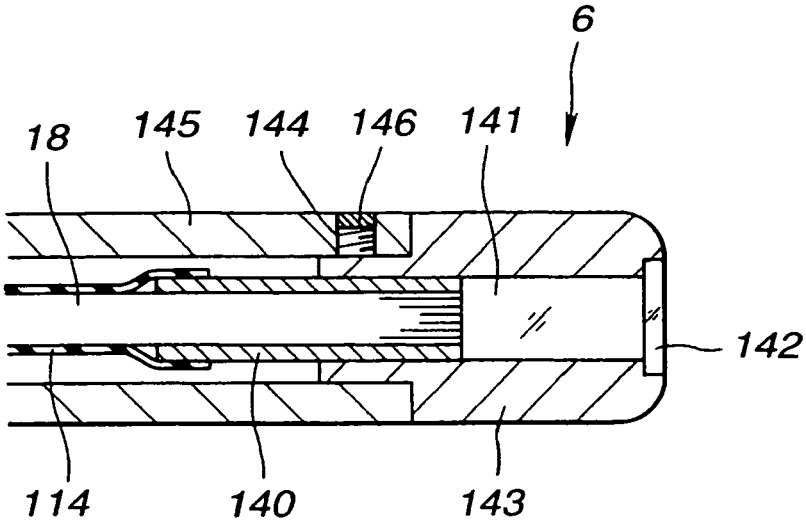
FIG. 21 is a longitudinal sectional view for explaining the structure of a light guide connector.

As shown in FIG. 21, the light guide connector 6 consists of a second light guide fiber frame 140, a rod lens 141, an incident end cover member 142, an incident end frame 143, and a connector base body 145. The second light guide fiber frame 140 made of a metal serves as an airtight partition member into which the proximal part of the light guide fiber bundle 18 is inserted. The rod lens 141 is located on the proximal end surface of the light guide fiber bundle 18, and homogenizes incident light falling on the light guide fiber bundle 18. The incident end cover member 142 made of sapphire serves as an airtight partition member located on the back end surface of the rod lens 141. The incident end frame 143 made of a metal serves as an airtight partition member accommodating the incident end frame 143 and others. The connector base body 145 is attached to the incident end frame 143 using a screw 144. The head of the screw 144 is covered with a filler 146 that is an adhesive for retaining watertightness.

The proximal part of the light guide fiber bundle 18 is, similarly to the aforesaid distal part thereof, unintermittently infiltrated with a molten glass. The outer circumference of the proximal part of the light guide fiber bundle 18 and the second light guide fiber frame 140 are joined hermetically by the molten glass.

Moreover, metal coating is, as mentioned above, performed on the lateral surface of the incident end cover member 142. The incident end cover member 142 and incident end frame 143 are hermetically joined by an airtight joining means.

Furthermore, the second light guide fiber frame 140 and incident end frame 143 are hermetically joined by performing laser welding.

Consequently, the portion enclosed with the incident end cover member 142, incident end frame 143, second light guide fiber frame 140, and end of the light guide fiber bundle 18 is hermetically sealed in the same manner as the hermetically sealed imaging unit body 100.

Consequently, the rod lens 141 lies in the hermetically sealed interior of the light guide connector 6. Even when a single fiber made of a multi-component glass or the like that is not resistive to high-pressure high-temperature steam is employed, it is unnecessary to concern about deterioration due to steam.

Moreover, the light guide fiber bundle 18 is sealed by the light guide fiber casing tube 114 and light guide fiber frames 111 and 140 at the first sealing level or higher. Generally, a silicon tube is adopted as the light guide fiber casing tube 114. However, in the present embodiment, a fluorocarbon resin tube is employed because it is less permeable to steam and more resistive to high-pressure high-temperature steam than the silicon tube. At this time, it must be checked whether the tube must be somewhat soft.

Now, the structure of a switch unit 13 will be described below.

Figure 22:
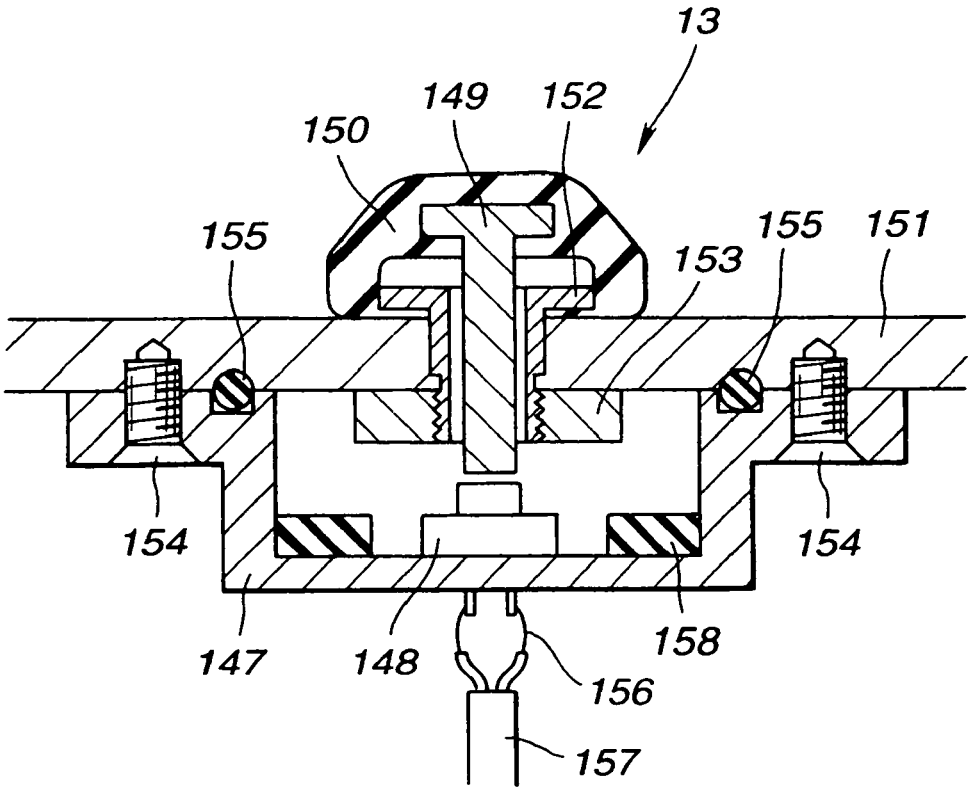
FIG. 22 is a sectional view for explaining the structure of a switch unit.

As shown in FIG. 22, the switch 13 consists of an electric switch 148, a presser pin 149, a switch cover 150, a presser member 152, a nut 153, screws 154, an O ring 155, and a switch cable 157. The electric switch 148 is an electronic part mounted in a package member 147, and designed compactly. The presser pin 149 is pressed in order to turn on or off the electric switch 148. The switch cover 150 is molded with the presser pin 149 inserted therein, and made of a rubber such as fluorine-contained rubber. The presser member 152 fixes the switch cover 150 to an operation unit housing 151 in a watertight manner. The presser pin 149 is passed through the presser member 152. The nut 153 is used to immobilize the presser member 152. The screws 154 are used to fix the package member 147 to the operation unit housing 147. The O ring 155 is used to attain watertightness between the package member 147 and housing 151. The switch cable 157 is spliced to a contact 156 of the electric switch 148. Consequently, the electric switch 148 lies in the space sealed at the first sealing level or higher using the switch cover 150 and O ring 155.

The switch cover 150 used to realize the sealed space is formed to be thick enough not to be burst or damaged even when the air in the sealed space expands or contracts due to decompression or pressurization performed during autoclaving.

The sealed space is pressure-resistant to resist decompression and pressurization performed during autoclaving. Moreover, the sealed space is much smaller than the internal space of the endoscope. An amount of air that expands due to decompression performed during autoclaving is therefore limited. As there exists a low possibility that the armor tube outlining the bendable part may burst as described in conjunction with the related art, there is also a low possibility that the switching cover 150 may burst. From this viewpoint, it is unnecessary to make the switch cover 150 too thick.

Aside from the switch unit 13, some portions of the internal endoscope space need not be sealed fully hermetically but must be sealed at a certain sealing level and protected from invasion of steam. These portions are, like the foregoing switch unit 13, sealed at the first sealing level or higher, whereby invasion of steam can be minimized successfully.

Moreover, a moisture absorptive member 158 may be placed in the sealed space. The moisture absorptive member 158 absorbs invading steam and will thus help prevent deterioration of electronic parts. If the moisture absorptive member can be replaced with a new one, it would be more advantageous.

The O ring 155 and other rubber sealing members are generally made of a silicon rubber or fluorine-contained rubber. However, a silicon rubber is quite permeable to steam. For this reason, the employment of the aforesaid sealing member made of a fluorine-contained rubber is preferred. For the same reason, a partition for a space that must be shielded from invasion of steam should be made of, for example, a fluorine-contained rubber rather than a silicon rubber. Likewise, a joint that must be shielded from invasion of steam should be realized using an epoxy adhesive or ceramic adhesive rather than a silicon adhesive.

A portion that cannot be hermetically sealed using an airtight partition member or airtight joining means for a dimensional or structural reason is covered with a gas barrier type coating. This will prove effective in hindering invasion of steam.

For example, the outer surface of the light guide fiber casing tube 114, the outer surface of the thermo-contractile tube of the imaging unit 17, and the other outer surfaces of joints formed with an adhesive may be covered with a gas barrier type coating. This will exert the advantage that an internal part, for example, the light guide fiber bundle 18 hardly deteriorates.

The coating methods of forming the gas barrier type coating include resin coating such as Parylene resin coating, metallic thin-film coating such as deposition-based coating or dip soldering-based coating, ceramic coating such as coating using silica into which silazane is converted, and crystal coating. For example, with the light guide fiber casing tube 114, a method of forming a soft coating must be adopted. According to this method, invasion of steam can be hindered without an increase in size of contents to be sealed. When the second sealing level can be attained according to the metallic thin-film coating, ceramic coating, or crystal coating, the method can be adopted for an observation optical system including optical members.

Similarly to the first embodiment, even when the endoscope of the present embodiment is autoclaved, the hermetically sealed imaging unit body 100 will not be destroyed, and steam will not invade into the interior of the hermetically sealed imaging unit body 100.

Moreover, according to the present embodiment, similarly to the hermetically sealed imaging unit body 100, the emission end portion and incidence end portion of the light guide unit 32, which are hermetically sealed and infiltrated with an airtight joining means, will not be destroyed. Moreover, steam will not invade into the light guide unit 82.

Furthermore, a switch unit 13 is sealed at the first sealing level or higher. Invasion of steam into the switch unit 13 is thus minimized. High-pressure high-temperature steam having invaded into the interior of the endoscope will not directly attack an electric switch.

Little steam having invaded will be absorbed by a moisture absorptive member 158. It will therefore be prevented that the electric switch 148 or the like fails due to steam or humidity. Moreover, high-pressure high-temperature steam will not directly attack a light guide fiber bundle 18 owing to the effect of an armor tube 35. Deterioration of a fiber glass can be prevented. This leads to a lowered possibility that a fiber may be broken.

In the present embodiment, almost all the contents of the endoscope that are susceptible to steam invading into the internal endoscope space are sealed in an airtight or watertight manner. This leads to a lowered possibility that the whole endoscope may fail.

The endoscope may be autoclaved without a non-return valve cap attached but with a vent in the outer wall of the endoscope left open in the same manner as it is sterilized as conventionally using an ethylene oxide gas. In this case, high-pressure high-temperature steam may invade actively into the interior of the endoscope. Nevertheless, since almost all the contents of the endoscope that are susceptible to steam, such as, an observing means, illuminating means, and switch unit are sealed in an airtight or watertight manner, the endoscope will not fail.

The present embodiment provides the advantages described below.

Even when a bendable endoscope having a housing member thereof made of a polymeric material is autoclaved, the armor tube of a bendable part will not burst and the functional parts incorporated in the endoscope will not fail.

Even when the endoscope is autoclaved, steam will not permeate through airtight partition members constituting a housing of a hermetically sealed imaging unit body, and joints of the hermetically joined airtight partition members. The steam will therefore not invade into the hermetically sealed imaging unit body. It is therefore prevented that electronic parts including a CCD will fail and that the quality of a view will be impaired due to condensation occurring on a lens.

Even when the endoscope is autoclaved, airtight partition members constituting a housing of a hermetically sealed objective unit and joints of the hermetically joined airtight partition members will not be destroyed. It will therefore not take place that steam invades into the interior of the hermetically sealed objective lens unit because of destruction. Needless to say, it will not take place that the electronic parts such as the CCD fail, and that the quality of a view is impaired due to condensation on a lens.

Even when the endoscope is autoclaved, steam will not invade into the hermetically sealed emission and incidence end portions of a light guide fiber bundle. Consequently, insufficient illumination stemming from condensation on a lens will not take place.

Even when the endoscope is autoclaved, high-pressure high-temperature steam having invaded into the internal endoscope space will not directly attack an electric switch. Moreover, little steam having invaded into a switch unit is absorbed by a moisture absorptive member. It will not take place that the electric switch fails due to steam or humidity.

Even when the endoscope is autoclaved, high-pressure high-temperature steam will not directly attack the light guide fiber bundle. This leads to a lowered possibility that fiber glasses may deteriorate to be broken.

During autoclaving, the internal endoscope space may be ventilated with outside air without a non-return valve cap attached in order to prevent burst of the armor tube of the bendable part. Even in this situation, the observation optical system, illumination optical system, switches, and other various contents of the endoscope will not fail.

Figure 23:
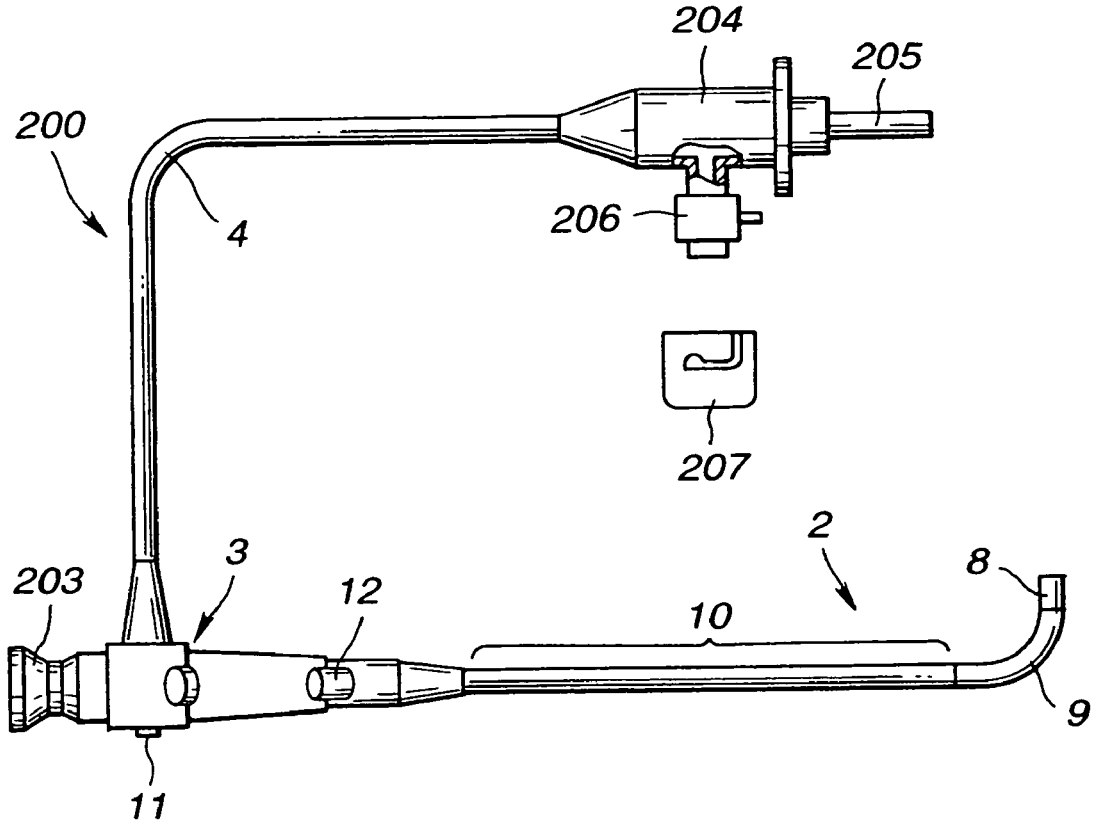
FIG. 23 to FIG. 25 relate to a third embodiment of the present invention.
Figure 24:
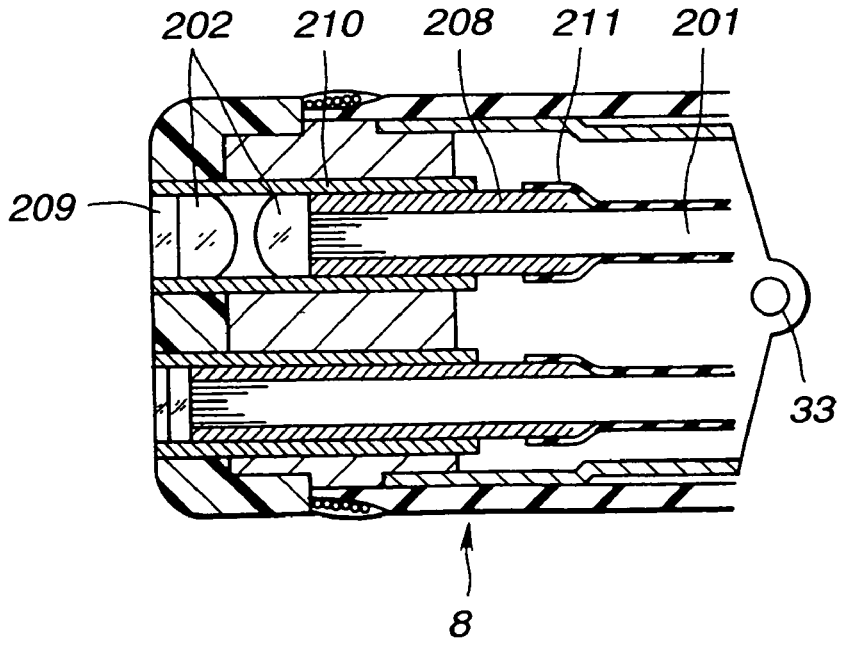
Figure 25:
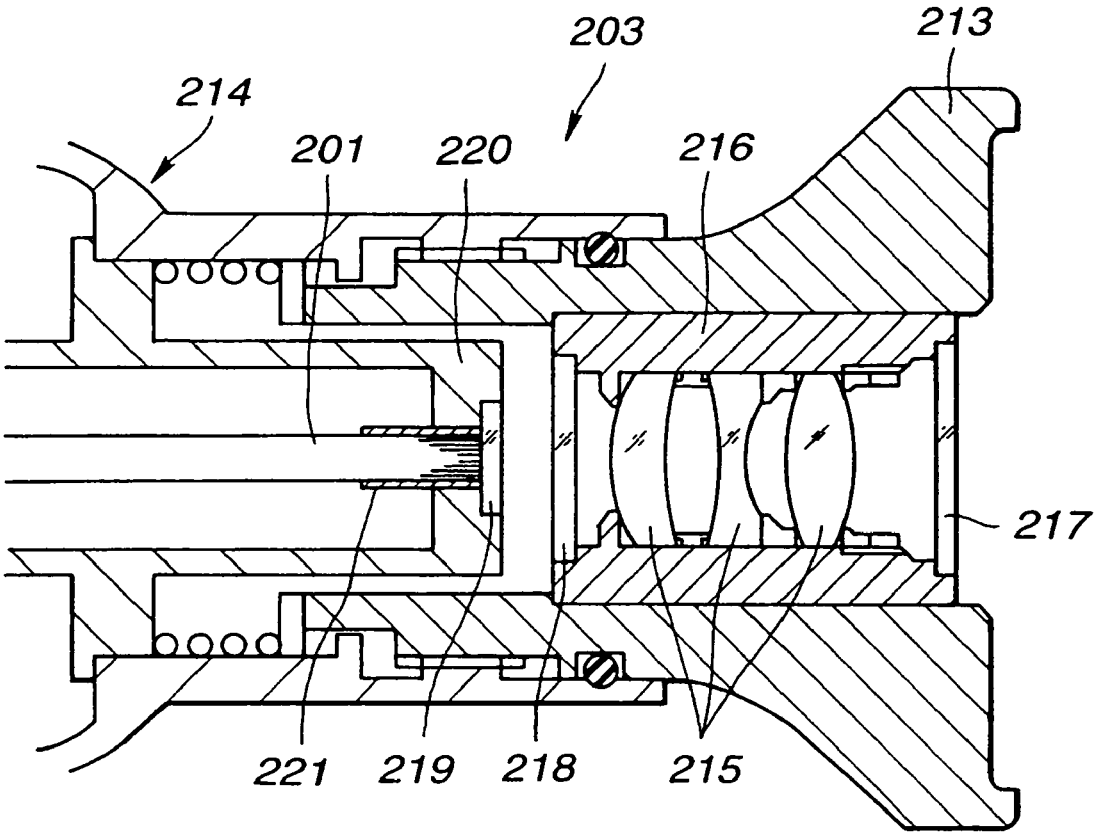

Referring to FIG. 23 to FIG. 25, the third embodiment of the present invention will be described below.

The structure of the present embodiment is substantially identical to that of the second embodiment. The same reference numerals will be assigned to identical components and only the description of the components different from those of the first and second embodiments will be described below.

An endoscope 200 in accordance with the present embodiment is, as shown in FIG. 23 and FIG. 24, a fiberscope employing fibers as an observing means, that is, an image transmitting means.

An image guide fiber bundle 201 lies through the insertion unit 2. The image guide fiber bundle 201 serving as an image transmission means is formed as an optical fiber bundle made by bundling fibers, that is, a plurality of optical fibers each having a core and cladding. Objectives 202 are located at the distal end of the image guide fiber bundle 201. An eyepiece unit 203 is located at the other end thereof.

A connector unit 204 has a light guide connector 205 and a ventilation base 206 through which outside air is circulated through the internal space of the endoscope 200. A ventilation cap 207 is mated with the ventilation base 206, whereby the interior of the endoscope 200 is ventilated with outside air.

Unlike the aforesaid embodiments, no imaging unit is incorporated in the distal part 8. Instead, an image guide fiber bundle 201, an image guide fiber frame 208, a group of objectives 202, an objective cover member 209, an objective lens frame 210, and an image guide fiber casing tube 211 are incorporated in the distal part 8. The image guide fiber frame 208, which is made of a metal, serves as an airtight partition member accommodating the image guide fiber bundle 201. The group of objectives 202 is located at the distal end of the image guide fiber bundle 201, and forms an object image. The objective cover member 209, which is made of sapphire serves as an airtight partition member located at the distal end of the group of objectives 202. The objective lens frame 210 made of a metal, serves as an airtight partition member accommodating the objective cover member and others. The image guide fiber casing tube 211 encases the image guide fiber bundle 201.

The fibers constituting the image guide fiber bundle 201 must be arranged in the same manner at the distal end and proximal end thereof. For this reason, both end portions of the fibers are immobilized while infiltrated with a glass that is melted with a fluid agent such as, an acid-dissolved glass. Therefore acid-dissolved glass fills the role of an airtightness retaining filler to be infiltrated into both end portions of the fibers constituting the image guide fiber bundle 201.

The distal part of the image guide fiber bundle 201 immobilized with the acid-dissolved glass and the image guide fiber frame 208 are, as described in relation to the second embodiment, hermetically joined using a molten glass. Moreover, a proximal lens included in the group of objectives 202 is bonded and fixed to the distal end of the image guide fiber bundle 201 using a transparent adhesive.

A metal coating is formed on the lateral surface of the objective cover member 209 and the inner circumference of the objective lens frame 210. The objective cover member 209 and objective lens frame 210 are hermetically joined by, for example, performing soldering.

A front lens included in the group of objectives 202 is locked in the objective lens frame 210 and hermetically united with the objective cover member 209. Thereafter, the image guide fiber bundle 201 to which a proximal lens included in the group of objectives 202 is fixed is inserted into the objective lens frame 210. The image guide fiber bundle 201 is then temporarily locked at a position, at which the group of objectives 202 comes into focus, by performing, for example, spot welding. Thereafter, the objective frame 210 and image guide fiber frame 208 are hermetically joined by performing laser welding.

Consequently, similarly to the hermetically sealed imaging unit body 100 in the second embodiment, the portion enclosed with the objective cover member 209, objective frame 210, image guide fiber frame 208 and end of the image guide fiber bundle 201 is, hermetically sealed.

Therefore, steam will not invade into the objective cover member 209 through gaps among the fibers and a gap between the image guide fiber bundle 201 and image guide fiber frame 208.

Any method other than a joining method using a molten glass may be adopted for joining the distal part of the image guide fiber bundle 201 immobilized with an acid-dissolved glass and the image guide fiber frame 208. For example, a metal coating may be formed on the outer circumference of the distal part of the image guide fiber bundle 201 immobilized with the acid-dissolved glass. The distal part of the image guide fiber bundle 201, which surface has been finished, and the image guide fiber frame 208 may be joined hermetically using a solder.

Moreover, the image guide fiber bundle 201 is not limited to a flexible fiber bundle having both end portions of the fibers immobilized with the acid-dissolved glass, and the intermediate portion of the fibers separated from one another with the acid-dissolved glass melted with a fluid agent. Each of the fibers has a core and cladding. Alternatively, a conduit fiber serving as one conduit over the whole length thereof and made by encapsulating a plurality of core glasses in cladding glasses will do. In this case, the cladding glass fills the role of an airtightness retaining filler for covering each core glass of an optical fiber.

In general, the flexible fiber bundle is made of a multi-component glass. The conduit fiber is made of a quartz glass as well as the multi-component glass.

As shown in FIG. 25, the eyepiece unit 203 consists of a group of eyepieces 215 and an eyepiece mount 213. The eyepiece unit 203 can be attached or detached to or from an endoscope body 214.

The group of eyepieces 215 is mounted in a hollow of a metallic eyepiece frame 216 serving as an airtightness partition member. A first eyepiece cover glass 217 and second eyepiece cover glass 218 are hermetically locked in the distal part and proximal part of the eyepiece frame 216 using, for example, a solder. The outer circumferences of the first and second eyepiece cover glasses 217 and 218, which are made of sapphire, and serving as airtight partition members are covered with a metal coating.

In other words, an internal space in which the group of eyepieces 215 is placed is sealed hermetically with the eyepiece frame 216, first eyepiece cover glass 217, and second eyepiece cover glass 218.

With the eyepiece unit 203 attached to the endoscope body 214, the first eyepiece cover glass 217 serves as an optical window that is included as part of a housing of the endoscope.

Furthermore, the proximal part of the image guide fiber bundle 201 lying through the endoscope body 214 has the same structure as the distal part of the aforesaid image guide fiber bundle 201.

Moreover, a metal coating is formed on the lateral surface of the cover glass 219. The cover glass 219 and fiber holding member 220 are hermetically joined by performing, for example, soldering. A second image guide fiber frame 221 and the fiber holding member 220 are hermetically joined using, for example, a solder.

Consequently, since the end of the image guide fiber bundle 201 is sealed hermetically, steam will not permeate through the end of the image guide fiber bundle 201 and the inner surface of the cover glass 219.

When the eyepiece unit 203 is not attached to the endoscope body 214, the cover glass 219 serves as an optical window that is part of the outer surface of the endoscope 200.

Moreover, the group of eyepieces 215 that is hermetically sealed can be freely attached or detached to or from the image output end of the image guide fiber bundle 201. Alternatively, similarly to the hermetically sealed objective unit 40 and the image input end of the CCD 43 employed in the first embodiment, the group of hermetically sealed eyepieces 215 may be closely bonded to the image output end of the image guide fiber bundle 201 by applying a transparent adhesive in such a manner that no air layer is present. In this case, an eyepiece focusing mechanism should be included in the hermetically sealed eyepiece unit 203 for the purpose of adjustment of the diopter of the eyepieces.

Moreover similar to the light guide fiber bundle 18 in the second embodiment, the image guide fiber bundle 201 is sealed at the first sealing level or higher level with a casing tube and base.

Operations to be exerted by the endoscope 200 having the foregoing structure will be described below.

When the ventilation cap 207 is mated with the ventilation base 206, the internal space of the endoscope 200 is ventilated with outside air. For cleaning, the ventilation cap 207 is not mated with the ventilation base 206 in order to attain watertightness. For autoclaving, the endoscope 200 is put in an autoclave with the ventilation cap 207 mated with the ventilation base 206. Thus, a burst of the armor tube 37 outlining the bendable part 9 is prevented.

At this time, a large amount of steam invades into the endoscope body 214 through the ventilation unit. Nevertheless, steam will not permeate through the distal end of the image guide fiber bundle 201 hermetically sealed in the endoscope body 214 and the group of eyepieces 215 included in the eyepiece unit 203 that can be attached or detached to or from the endoscope body 214. Therefore, steam will not invade into the sealed spaces and produce water droplets on optical members.

The present embodiment has the advantages described below.

When a bendable endoscope whose housing member is made of a polymeric material is autoclaved, it will not take place that the armor tube of a bendable part bursts and that a field of view is narrowed.

When the endoscope is autoclaved, steam will not invade into the hermetically sealed distal part of an image guide fiber bundle and an eyepiece unit. Moreover, when water droplets are produced on the surface of the cover glass of the eyepiece unit, the eyepiece unit can be detached in order to wipe off the water droplets. Consequently, a field of view provided by the eyepiece unit will not be narrowed due to condensation occurring on a lens.

When the endoscope is autoclaved, the hermetically sealed distal part of the image guide fiber bundle, airtight partition members constituting the housing of the eyepiece unit, and joints of the hermetically joined airtight partition members will not be destroyed by not take place that due to destruction. Naturally, the field of view will not be narrowed due to condensation on a lens.

When the endoscope is autoclaved, high-pressure high-temperature steam will not directly attack the image guide fiber bundle. Consequently, fiber glasses will not deteriorate and break.

According to the present embodiment, instead of the ventilation cap, 207 a cap member having the capability of a non-return valve may be, similarly to the non-return valve cap 20 in the first embodiment, mated with the ventilation base 206.

In this case, the cap member must be designed so that when it is mated with the ventilation base 206, it will communicate with an outside and works as a non-return valve. When this structure is adopted, similar to the first embodiment, steam will not, actively invade into the interior of the endoscope 200 during autoclaving and will prevent the contents of the endoscope 200 from deteriorating.

Figure 26:
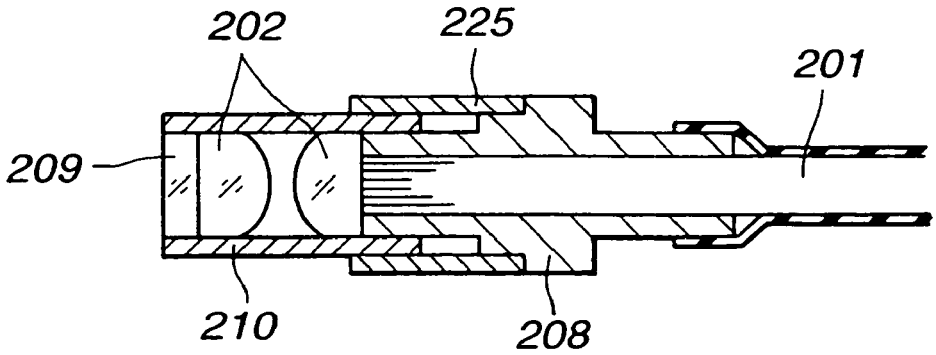
FIG. 26 is an explanatory diagram concerning another joined state of an objective frame and image guide fiber frame.

Moreover, according to the present embodiment, the objective frame 210 and image guide fiber frame 208 are hermetically joined by performing laser welding. Alternatively, as shown in FIG. 26, similarly to the airtightness retaining pipe 87 in the second embodiment, an airtightness retaining member 225 made of a metal, ceramic, or the like may be employed. The airtightness retaining member 225, the objective frame 210, and image guide fiber frame 208 may be hermetically joined by performing laser welding or soldering. In this case, the objective frame 210 and image guide fiber frame 208 can be bonded more firmly to each other. Consequently, it becomes easy to bring the group of objectives 202 into focus during assembling.

Moreover, when moisture condenses into water droplets on the surface of the cover glass 219 during autoclaving, or when water droplets are produced on the surface of the second cover glass 218, the water droplets can be wiped off easily by removing the eyepiece unit 203.

Figure 27:
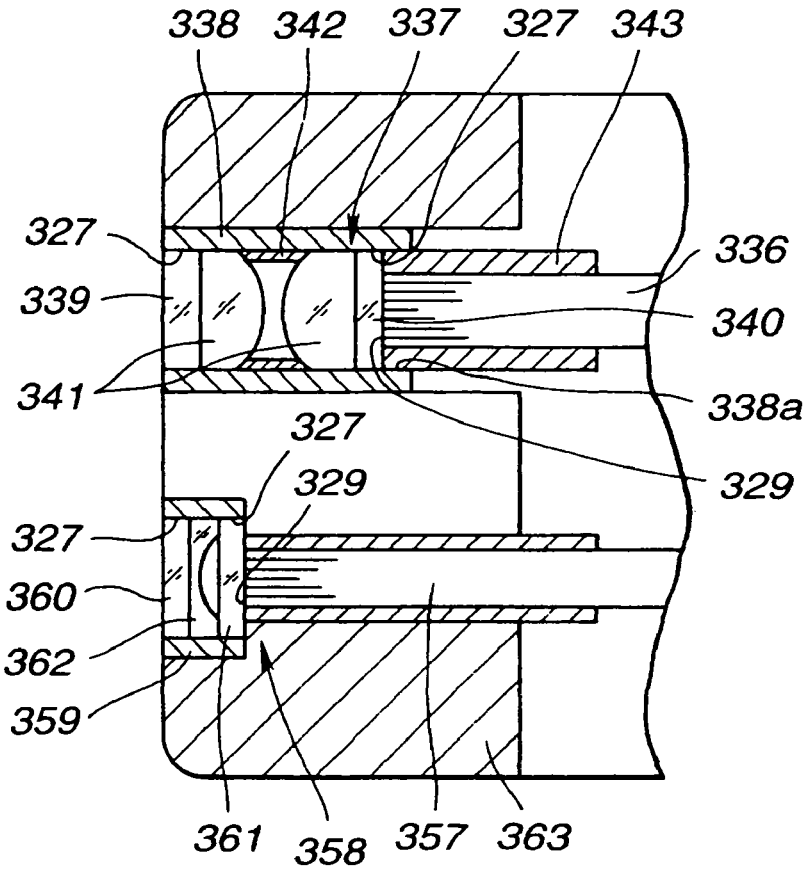
FIG. 27 is a longitudinal sectional view for explaining another structure of the distal part of an endoscope and its neighborhood.

As shown in FIG. 27, a hermetically sealed objective unit 337 may be firmly bonded to the distal end of an image guide fiber bundle 336, that is, the image input end thereof using a transparent adhesive 329 in such a manner that no air layer is present. The objective unit 337 consists of an objective frame 338, a distal cover glass 339, a back-end cover glass 340, a group of objectives 341, and a spacer ring 342. The objective frame 338 is made of a metal. The distal cover glass 339, which is made of sapphire, is hermetically locked in the distal part of the objective frame 338 by performing brazing or the like. A metal coating is formed on the outer circumference between the distal cover glass 339 as a joint of the distal cover glass 339 and objective frame 338. The group of objectives 341 is placed in a space hermetically sealed with the objective frame 338, and cover glasses 339 and 340.

In the structure, the spacer ring 342 is used to position the group of objectives 341 and to focus it on the image input end of the image guide fiber bundle 336. Therefore, particularly during assembling, focusing does not need to be performed.

The back-end cover glass 340 is not fixed to the proximal end of the objective frame 338 but secured with an engagement portion 338a left at the end of the objective frame 338. The distal part of a base 343 of the image guide fiber bundle 336 is inserted and fixed to the engagement portion 338 a formed at the end of the objective frame 338. Owing to the structure, the center axis of the group of objectives 341 is aligned with the center axis of the image guide fiber bundle 336.

Furthermore, in the present embodiment, a hermetically sealed illumination lens unit 358 is, as shown in FIG. 27, closely fixed to the emission end of a light guide fiber bundle 357 using a transparent adhesive 329 in such a manner that no air layer is present. The illumination lens unit 358 consists of an illumination frame 359, a distal illumination cover glass 360, a back-end illumination cover glass 361, and an illumination lens 362. The illumination frame 359 is made of a metal. The distal illumination cover glass 360, which is made of sapphire, is hermetically locked in the distal part of the illumination frame 359 by performing, for example, brazing. A metal coating is formed on the outer circumference of the distal illumination cover glass 360 as a joint of the distal illumination cover glass 360 and the illumination frame 359. The back-end illumination cover glass 361 made of sapphire, is hermetically locked in the proximal part of the illumination frame 359. The illumination lens 362 is placed in a space hermetically sealed by the illumination frame 359 and cover glasses 360 and 361.

The light guide fiber bundle 357 and the illumination lens unit 358 are locked in a mounting hole bored in a distal structure of an insertion unit 2. At this time, the light guide fiber bundle 357 is inserted through the back end of the hole, while the illumination lens unit 358 is inserted through the front end thereof.

Figure 28:
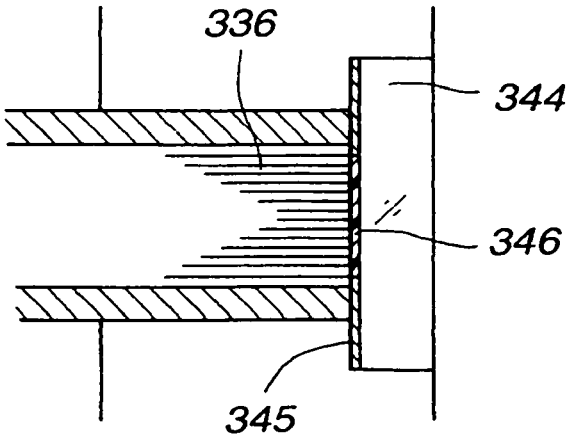
FIG. 28 is an explanatory diagram concerning an image output end of an image guide fiber bundle to which a mask deposition cover glass is fixed.
Figure 29:
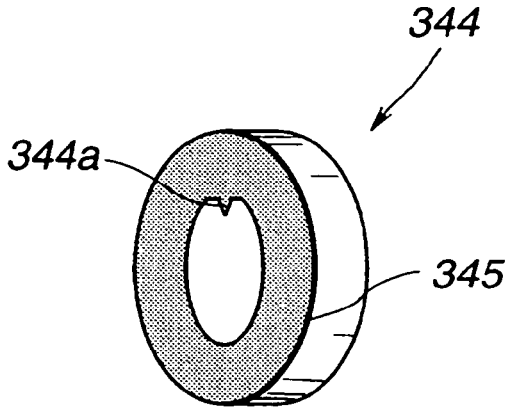
FIG. 29 is a perspective view for explaining the mask deposition cover glass.

As shown in FIG. 28, a mask deposition cover glass 344 is fixed to the image output end of the image guide fiber bundle 336 using a transparent silicon adhesive 346 in such a manner that no air layer is present. As shown in FIG. 29, a black deposition material 345 such as chromium oxide is deposited on the mask deposition cover glass 344, thus forming a field mask. A portion of the mask deposition cover glass 344 on which the deposition material 345 is not deposited defines a range of a field of view seen by an observer. The field mask has an up indicator 344a to help the observer recognize an up direction.

Figure 30:
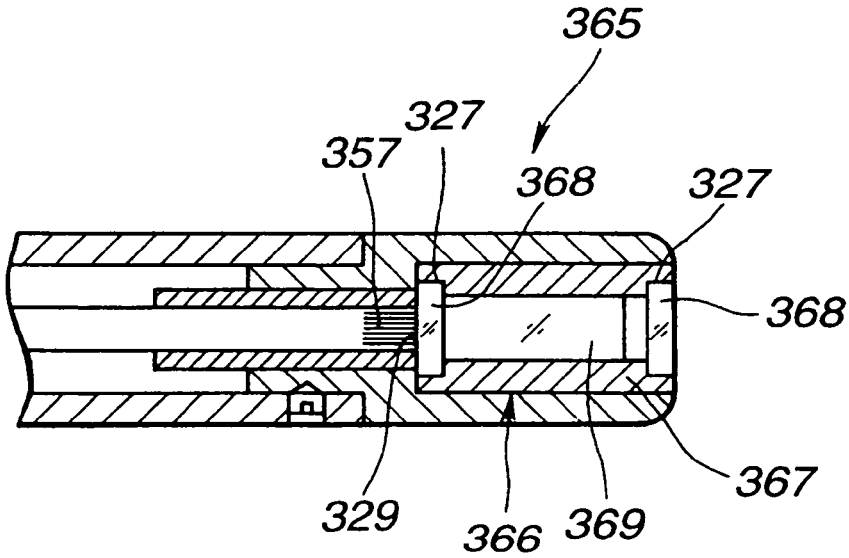
FIG. 30 is an explanatory diagram concerning a connector unit coupled to a light source apparatus.

FIG. 30 shows a connector unit 365 to be coupled to a light source apparatus. A hermetically sealed illumination light incidence end optical member unit 366 is closely fixed to the incidence end of the light guide fiber bundle 357 using a transparent adhesive 329 in such a manner that no air layer is present.

The illumination light incidence end optical member unit 366 consists of a rod lens frame 367, two cover glasses 368, and a rod lens 369. The rod lens frame 367 is made of a metal. The two cover glasses 368 made of sapphire are hermetically locked in both the end portions of the rod lens frame 267 by performing brazing or the like. A metal coating is formed on the outer circumferences of the cover glasses 368 as joints of the cover glasses 368 and the rod lens frame 367. The rod lens 369 is placed in a space hermetically sealed with the rod lens frame 367 and cover glasses 368. The rod lens 369 is formed with a single fiber made of a multi-component glass, and homogeneously disperses incident light emanating from a light source.

In FIG. 27 and FIG. 30, reference numeral 327 denotes the joints at which the lenses and frames are hermetically joined by performing brazing, soldering, or metal welding such as laser welding.

Assuming that the endoscope having the foregoing structure is autoclaved using high-pressure high-temperature steam, steam invades into the interior of the endoscope through the O rings, adhesives, resin parts, or the like. However, since the objective unit 337 located at the image input end of the image guide fiber bundle 336 is hermetically sealed, steam will not invade into the hermetically sealed space. Consequently, water droplets will not be produced on optical members including the group of objectives 341 to eventually cloud them.

Moreover, the light guide fiber bundle 336 and back-end cover glass 340 are closely fixed to each other using the transparent adhesive 329 in such a manner that no air layer is present. Moisture will therefore not condense into water droplets between the light guide fiber bundle 357 and back-end cover glass 361. Furthermore, the mask deposition cover glass 344 is closely fixed to the image output end of the image guide fiber bundle 336 using the transparent adhesive 329 in such a manner that no air layer is present. Moisture will not condense into water droplets between the mask deposition cover glass and image guide fiber.

Furthermore, the illumination lens unit 358 located at the emission end of the light guide bundle 357 is sealed hermetically. Water droplets will therefore not be produced to cloud the optical members including the illumination lens 362. Moreover, the light guide fiber bundle 357 and back-end illumination cover glass 361 are closely fixed to each other using the transparent adhesive 329 in such a manner that no air layer is present. Moisture will therefore not condense into water droplets between the light guide fiber bundle 357 and back-end, illumination cover glass 361. Furthermore, the illumination light incidence end lens unit 366 located at the incidence end of the light guide fiber bundle 357 is hermetically sealed. Steam will therefore not invade into the hermetically sealed space and water droplets will not be produced on the optical members including the rod lens 369 to eventually cloud the optical members. Moreover, the light guide fiber bundle 357 and cover glass 368 are closely fixed to each other using the transparent adhesive 329 in such a manner that no air layer is present. Consequently, moisture will not condense into water droplets between the light guide fiber bundle 357 and cover glass 368.

The present embodiment is expected to provide the advantages described below.

Even when an endoscope is autoclaved, it will not take place that optical members included in an objective unit and an eyepiece unit are clouded or a field of view is narrowed due to deterioration of lens glasses. The objective unit and the eyepiece unit are hermetically sealed and located at the image input end of an image guide fiber bundle and the image output end thereof respectively.

Moreover, even when the endoscope is autoclaved, there is no fear that moisture may condense into water droplets between the end of the image guide fiber bundle and an optical member. This is because optical members are closely fixed to the image input end and image output end of the image guide fiber bundle in such a manner that no air layer is present.

Furthermore, even when the endoscope is autoclaved, the optical members locked in the spaces hermetically sealed at the emission end and incidence end of a light guide fiber bundle will not be clouded, or lens glasses will not deteriorate. Consequently, it will not take place that illumination light diminishes or light is distributed in an inhomogeneous manner.

Moreover, even when the endoscope is autoclaved, moisture will not condense into water droplets between the ends of the light guide fiber bundle and the optical members. This is because the optical members are closely fixed to the incidence end and emission end of the light guide fiber bundle in such a manner that no air layer is present. Consequently, it will not take place that illumination light diminishes and light is distributed in an inhomogeneous manner.

Furthermore, the image output end of the image guide fiber bundle and a mask deposition cover glass are closely fixed to each other in such a manner that no air layer is present. Interference fringes stemming from reflection occurring between the image output end and mask deposition cover glass will not be produced.

Furthermore, the mask deposition cover glass is bonded to the image output end of the image guide fiber bundle using a silicon adhesive that can be wiped off relatively easily. The mask deposition cover glass can therefore be repaired readily.

According to the present invention, it is apparent that a wide range of different embodiments can be constructed based on the invention without a departure from the spirit and scope of the invention. The present invention will be limited by the appended claims but not be restricted by any specific embodiments.

What is claimed is:

1. An endoscope capable of being autoclaved, comprising:

an outer casing of the endoscope made at least partially of a polymeric material and having an interior; and a component housed in the interior of the outer casing and constituted as a hermetically sealed unit composed of a plurality of airtight partition members, end parts of said plurality of airtight partition members being hermetically joined to one another such as to at least partially have said partition members overlap one another thereby to provide an airtight space;

wherein the outer casing is formed to provide a first sealing level to hinder liquid from invading into the interior thereof while permitting high-pressure, high-temperature steam given off during autoclaving to invade into the interior thereof; and the component is formed to provide a second sealing level higher than the first sealing level of the outer casing, to hinder the high-pressure, high-temperature steam penetrating through the outer casing during autoclaving from invading into the interior,

*wherein said hermetically sealed unit includes at least one of optical members and electronic parts or both said optical members and said electronic parts as airtight partition members, and*

*wherein said hermetically sealed unit is a lens unit having optical members as said airtight partition members, said lens unit having a first and second end portions which are hermetically locked as optical windows*.

2. An endoscope capable of being autoclaved according to claim 1, wherein said airtight partition members are members made of a metal, ceramic, glass, or crystalline material.

3. An endoscope capable of being autoclaved according to claim 1, wherein said hermetically sealed unit is composed of a plurality of airtight partition members said airtight partition members are hermetically joined to one another at one or more joints, said joints are made of a metal, ceramic, glass, or crystalline material.

4. An endoscope capable of being autoclaved according to claim 3, wherein said airtight joining means is a joint formed by welding carried out by one of fusion welding, pressure welding, brazing, soldering or joining using molten glass.

5. An endoscope capable of being autoclaved according to claim 1, wherein said hermetically sealed unit formed at said second sealing level is pressure-resistant to resist a negative pressure or pressurization to be attained or performed during autoclaving so as not to be destroyed, and wherein said hermetically sealed unit is sealed to such an extent that high-pressure high-temperature steam given off during autoclaving will not invade into an interior of said hermetically sealed unit.

[6. An endoscope capable of being autoclaved according to claim 1, wherein said hermetically sealed unit includes at least one of optical members and electronic parts or both said optical members and said electronic parts as airtight partition members.]

[7. An endoscope capable of being autoclaved according to claim 6, wherein said hermetically sealed unit is a lens unit having optical members as said airtight partition members, said lens unit having a first and second end portions which are hermetically locked as optical windows.]

8. An endoscope capable of being autoclaved according to claim 7, wherein a metal coating having a lowermost layer formed as a low reflectance layer and an uppermost layer formed as a joining layer formed on the outer circumferences of said optical members included in said lens unit.

9. An endoscope capable of being autoclaved according to claim 8, wherein said low reflectance layer has a two-layer structure consisting of a lower layer made of chromium oxide and an upper layer made of chromium.

10. An endoscope capable of being autoclaved according to claim 8, wherein said outer circumferences of said optical members on which said low reflectance layer is formed are polished so that an average roughness (Ra) will fall within a range of 0.1 μm to 1 μm and the largest roughness (Pv) will fall within a range of 2 μm to 5 μm.

11. An endoscope capable of being autoclaved according to claim 7, comprising an observing means having an optical fiber bundle as a light introducing path, said optical fiber bundle has an input end and an output end, and said lens unit is located at one of said input end and output end of said optical fiber bundle.

12. An endoscope capable of being autoclaved according to claim 11, wherein one of said optical members included in said lens unit is coupled to one of said input end and output end of said optical fiber bundle.

13. An endoscope capable of being autoclaved according to claim 11, wherein said lens unit located at one of said input end and output end of said optical fiber bundle is detachable.

14. An endoscope capable of being autoclaved according to claim 6, wherein said hermetically sealed unit includes an observing means having an optical member as said airtight partition member, said optical member is hermetically locked as an optical window therein, and said optical window is bared on an outer surface forming part of said outer casing of said endoscope.

15. An endoscope capable of being autoclaved according to claim 14, wherein said observing means is an imaging unit having a solid-state imaging device as part of an image transmitting means, said solid-state imaging device having an image input end, and an objective unit having a first and second end portions which are hermetically locked as optical windows, said objective unit is located at said image input end of said solid-state imaging device.

16. An endoscope capable of being autoclaved according to claim 15, wherein one of said optical windows included in said objective unit is placed in contact with a image input end of said solid-state imaging device.

17. An endoscope capable of being autoclaved according to claim 16, wherein said optical window and said image input end of said solid-state imaging device are joined using a transparent adhesive.

18. An endoscope capable of being autoclaved according to claim 15, wherein said hermetically sealed unit is accommodated in said objective unit, said objective unit forms an object image, said object image is projected on said imaging surface of said solid-state imaging device, said objective unit is located in front of said imaging surface of said solid-state imaging device, and a member opposed to a proximal outer surface of said solid-state imaging device is sealed at said first sealing level.

19. An endoscope capable of being autoclaved according to claim 14, comprising an insertion unit having a bendable part and a distal rigid part, said bendable part being in gaseous communication with said distal rigid part of said insertion unit, said hermetically sealed unit is accommodated in said insertion unit and positioned within said distal rigid part distal to said bendable part.

20. An endoscope capable of being autoclaved according to claim 6, comprising an observing means having an optical fiber bundle as a light introducing path, said optical fiber bundle has an input end portion and an output end portion, said end portions of said optical fiber bundle are infiltrated with an airtightness retaining filler to make said optical fibers airtight, and wherein said end portions of said optical fiber bundle are hermetically fixed to said airtight partition members of said hermetically sealed unit.

21. An endoscope capable of being autoclaved according to claim 6, wherein one of the airtight partition members of the hermetically sealed unit is a first optical member, the first optical member engages with a frame member and has a distal surface, and wherein when a second optical member is fixed to only the distal surface of the first optical member, the second optical member is not engaged with the frame member.

22. An endoscope capable of being autoclaved according to claim 1, comprising an insertion unit having a bendable part and a distal rigid part, and an operation unit, said bendable part of said insertion unit is coupled to said operation unit, said bendable part of said insertion unit is in gaseous communication with said distal rigid part of said insertion unit, a first hermetically sealed unit is included in said distal rigid part of said insertion unit distal to said bendable part of said insertion unit, a second hermetically sealed unit is located in said operation unit, and said first and second hermetically sealed units are electrically linked by a cable.

23. An endoscope capable of being autoclaved according to claim 1, wherein one of said first and second sections being an insertion unit whose outer casing is made at least partially of a polymeric material.

24. An endoscope capable of being autoclaved according to claim 1, wherein said first sealing level seals said internal spaces of said first and second sections in a watertight manner relative to said ambient space surrounding said outer casing.

25. An endoscope capable of being autoclaved according to claim 1, wherein even when a high-pressure steam permeates through said first sealing level and invades into said internal spaces of said sections, said high-pressure high-temperature steam will be hindered from invading into said hermetically sealing unit formed at said second sealing level.

26. An endoscope capable of being autoclaved according to claim 23, wherein the component is composed of a plurality of airtight partition members which are hermetically joined to one another by an airtight joining means.

27. An endoscope capable of being autoclaved according to claim 26, wherein said airtight joining means comprises:

locking parts respectively provided on the plurality of airtight partition members at positions to hermetically join the plurality of airtight partition members to one another;

a coating part formed by having a metal or glass coating formed on at least one of the locking parts provided on the plurality of airtight partition members; and airtight joining part formed by heating the joined part of the airtight partition members to fuse the coating part.

28. An endoscope capable of being autoclaved, comprising:

an outer casing means made at least partially of a polymeric material that secures an internal space;

a component housed in the internal space of the outer casing means and constituted as a hermetically sealed unit composed of a plurality of airtight partition members, end parts of said plurality of airtight partition members being hermetically joined to one another such as to at least partially have said partition members overlap one another thereby to provide an airtight space;

a first sealing means, with which the outer casing means is provided, to provide the outer casing means with watertightness to hinder liquid from invading into the interior of the outer casing means and to provide a first sealing level to permit high-pressure, high-temperature steam given off during autoclaving to invade into the internal space of the outer casing means; and a second sealing means with which the component is provided, to provide the component with a second sealing level higher than the first sealing level provided by the first sealing means, to hinder the high-pressure, high-temperature steam invading through the outer casing means during autoclaving from invading into the airtight partition members,

*wherein said hermetically sealed unit includes at least one of optical members and electronic parts or both said optical members and said electronic parts as airtight partition members, and*

*wherein said hermetically sealed unit is a lens unit having optical members as said airtight partition members, said lens unit having a first and second end portions which are hermetically locked as optical windows.*

*29. An endoscope capable of being autoclaved, comprising:*

*an outer casing made at least partially of a polymeric material and having an interior;*

*a component housed in the interior of the outer casing and constituted as a hermetically sealed unit composed of a plurality of airtight partition members which are hermetically joined to one another and at least partially overlapped;*

*a frame body which constitutes an end of the component;*

*a first optical member which is hermetically locked in the frame body and which forms an optical path; and*

*a second optical member which is positioned, bonded and fixed to a distal surface of the first optical member and which forms the optical path,*

*wherein*

*the outer casing is formed to provide a first sealing level to hinder liquid from invading into the interior thereof while permitting high-pressure, high-temperature steam given off during autoclaving to invade into the interior thereof; and*

*the component is formed to provide a second sealing level higher than the first sealing level of the outer casing, to hinder the high-pressure, high-temperature steam penetrating through the outer casing during autoclaving from invading into the interior.*

*30. An endoscope according to claim 29,*

*wherein the second optical member has an outer configuration of a dimension that leaves a predetermined gap*

*between an outer circumference of the second optical member and an inner circumference of the frame body.*

*31. An endoscope according to claim 29,*

*wherein the second optical member is positioned, bonded and fixed to a distal surface of the first optical member.*

*32. An endoscope comprising:*

*an outer casing made at least partially of a polymeric material and having an interior;*

*a component housed in the interior of the outer casing and constituted as a hermetically sealed unit composed of a plurality of airtight partition members which are hermetically joined to one another and at least partially overlapped;*

*a frame body defining an airtight inner space, the frame body being capable of expanding when subjected to autoclaving, while maintaining the airtightness of the inner space;*

*an optical window coupled to the frame body to guide light into the inner space;*

*a first optical member having a first diameter and mounted within the airtight inner space and disposed on an optical axis of incident light penetrating through the optical window;*

*a second optical member mounted within the inner space without contacting any portion of the frame body in a manner whereby expansion and contraction of the second optical member does not affect the ability of the frame body to maintain the airtightness of the inner space*

*wherein*

*the outer casing is formed to provide a first sealing level to hinder liquid from invading into the interior thereof while permitting high-pressure, high-temperature steam given off during autoclaving to invade into the interior thereof; and*

*the component is formed to provide a second sealing level higher than the first sealing level of the outer casing, to hinder the high-pressure, high-temperature steam penetrating through the outer casing during autoclaving from invading into the interior.*

*33. An endoscope according to claim 32, in which the frame body comprises a plurality of frame body sections that are arranged following one another along the optical axis, the frame body sections including a distal frame section, and a second frame section.*

*34. An endoscope according to claim 33, further comprising an isolating frame section disposed between and coupling the distal frame section and the second frame section.*

*35. An endoscope according to claim 34, in which the frame sections are made of the same material.*

*36. An endoscope according to claim 34, in which a material of the distal frame section and the second frame section is metal.*

*37. An endoscope according to claim 34, further comprising a lens arrangement and a lens frame surrounding the lens arrangement and disposed in the inner space.*

*38. An endoscope according to claim 37, in which the lens arrangement and its lens frame is disposed adjacent the distal frame section.*

*39. An endoscope according to claim 38, in which the lens frame contacts a portion of the isolating frame and comprises a section that is juxtaposed to a portion of the distal frame with an airspace therebetween.*

*40. An endoscope according to claim 32, further comprising adhesive material filling a portion of the inner space and disposed in a region which partially contacts the first optical member.*

* * * * *